United States Patent
Chen et al.

(10) Patent No.: US 6,660,903 B1
(45) Date of Patent: *Dec. 9, 2003

(54) CENTER-FILL ABSORBENT ARTICLE WITH A CENTRAL RISING MEMBER

(75) Inventors: Fung-jou Chen, Appleton, WI (US); Jeffrey Dean Lindsay, Appleton, WI (US); Julie Marie Bednarz, Neenah, WI (US); Joseph DiPalma, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/411,258

(22) Filed: Oct. 1, 1999

(51) Int. Cl.[7] ............................. A61F 13/15; A61F 13/20
(52) U.S. Cl. ....................................................... 604/378
(58) Field of Search ................................ 604/358, 367, 604/369, 374, 378, 380, 385.01, 385.101, 385.12, 389, 385.17

(56) References Cited

U.S. PATENT DOCUMENTS

| | | |
|---|---|---|
| 2,064,431 A | 12/1936 | Jurgensen |
| 2,683,457 A | 7/1954 | Cunningham |
| 2,747,575 A | 5/1956 | Mercer |
| 3,126,888 A | 3/1964 | Woldman |
| 3,156,242 A | 11/1964 | Crowe, Jr. |
| 3,294,091 A | 12/1966 | Morse |
| 3,575,174 A | 4/1971 | Mogor |
| 3,667,466 A | 6/1972 | Ralph |
| 3,860,003 A | 1/1975 | Buell |
| 3,881,489 A | 5/1975 | Hartwell |
| 3,881,491 A | 5/1975 | Whyte |
| 3,921,232 A | 11/1975 | Whyte |
| 3,989,867 A | 11/1976 | Sisson |
| 4,015,604 A | 4/1977 | Csillag |
| 4,100,324 A | 7/1978 | Anderson et al. |
| 4,195,634 A | 4/1980 | DiSalvo et al. |
| 4,247,362 A | 1/1981 | Williams |
| 4,285,343 A | 8/1981 | McNair |

(List continued on next page.)

FOREIGN PATENT DOCUMENTS

| | | |
|---|---|---|
| AU | 699325 | 12/1998 |
| CA | 884608 | 11/1971 |
| DE | 196 40 451 A1 | 4/1998 |
| EP | 0136524 A1 | 4/1985 |
| EP | 0360285 A2 | 3/1990 |
| EP | 0 400 895 A1 | 12/1990 |

(List continued on next page.)

OTHER PUBLICATIONS

AATCC Test Method 127–1977, "Water Resistance: Hydrostatic Pressure Test," Technical Manual of the American Association of Textile Chemists and Colorists, reaffirmed 1977, p. 242.

(List continued on next page.)

Primary Examiner—Weilun Lo
Assistant Examiner—Michele Kidwell
(74) Attorney, Agent, or Firm—Pauley Petersen Kinne & Erickson

(57) ABSTRACT

An absorbent article is disclosed comprising a central absorbent member, an outer absorbent member, and a central rising member for urging the central absorbent member toward the body of the user when compressed laterally inward by the legs of the user. The article is able to achieve good center-fill performance when in use and maintain excellent body fit.

72 Claims, 10 Drawing Sheets

U.S. PATENT DOCUMENTS

| | | |
|---|---|---|
| 4,324,246 A | 4/1982 | Mullane et al. |
| 4,342,314 A | 8/1982 | Radel et al. |
| 4,397,644 A | 8/1983 | Matthews et al. |
| 4,405,326 A | 9/1983 | Lenaghan |
| 4,421,812 A | 12/1983 | Plant |
| 4,425,130 A | 1/1984 | DesMarais |
| 4,463,045 A | 7/1984 | Ahr et al. |
| 4,476,180 A | 10/1984 | Wnuk |
| 4,480,516 A | 11/1984 | Leroy |
| 4,490,147 A | 12/1984 | Pierce et al. |
| 4,496,359 A | 1/1985 | Pigneul |
| 4,536,181 A | 8/1985 | Cook |
| 4,556,146 A | 12/1985 | Swanson et al. |
| 4,556,560 A | 12/1985 | Buckingham |
| 4,573,986 A | 3/1986 | Minetola et al. |
| 4,576,596 A | 3/1986 | Jackson et al. |
| 4,576,597 A | 3/1986 | Hlaban et al. |
| 4,578,070 A | 3/1986 | Holtman |
| 4,589,876 A | 5/1986 | Van Tilburg |
| 4,608,047 A | 8/1986 | Mattingly |
| 4,654,040 A | 3/1987 | Luceri |
| 4,655,759 A | 4/1987 | Romans-Hess et al. |
| 4,662,876 A | 5/1987 | Wiegner |
| 4,687,478 A | 8/1987 | Van Tileburg |
| 4,701,177 A | 10/1987 | Ellis et al. |
| RE32,649 E | 4/1988 | Brandt et al. |
| 4,738,677 A | 4/1988 | Foreman |
| 4,753,644 A | 6/1988 | Cottenden et al. |
| 4,758,240 A | 7/1988 | Glassman |
| 4,804,380 A | 2/1989 | Lassen et al. |
| 4,846,824 A | 7/1989 | Lassen et al. |
| 4,879,170 A | 11/1989 | Radwanski et al. |
| 4,886,513 A | 12/1989 | Mason, Jr. et al. |
| 4,936,839 A | 6/1990 | Molee et al. |
| 4,950,264 A | 8/1990 | Osborn, III |
| 4,961,736 A | 10/1990 | McCloud |
| 4,964,857 A | 10/1990 | Osborn |
| 4,973,325 A | 11/1990 | Sherrod et al. |
| 5,007,906 A | 4/1991 | Osborn, III et al. |
| 5,009,653 A | 4/1991 | Osborn, III |
| 5,030,314 A | 7/1991 | Lang |
| 5,147,343 A | 9/1992 | Kellenberger |
| 5,147,345 A | 9/1992 | Young et al. |
| 5,151,092 A | 9/1992 | Buell et al. |
| 5,188,625 A | 2/1993 | Van Iten et al. |
| 5,217,445 A | 6/1993 | Young et al. |
| 5,217,447 A | 6/1993 | Gagnon |
| 5,219,342 A | 6/1993 | Hatch et al. |
| 5,235,515 A | 8/1993 | Ungpiyakul et al. |
| 5,236,428 A | 8/1993 | Zajaczkowski |
| 5,267,992 A | 12/1993 | Van Tilburg |
| 5,300,055 A | 4/1994 | Buell |
| 5,308,346 A | 5/1994 | Sneller et al. |
| 5,324,278 A | 6/1994 | Visscher et al. |
| 5,324,575 A | 6/1994 | Sultze et al. |
| 5,342,337 A | 8/1994 | Runeman et al. |
| 5,342,342 A | 8/1994 | Kitaoka |
| 5,350,624 A | 9/1994 | Georger et al. |
| 5,354,400 A | 10/1994 | Lavash et al. |
| 5,360,420 A | 11/1994 | Cook et al. |
| 5,389,094 A | 2/1995 | Lavash et al. |
| 5,399,175 A | 3/1995 | Glaug et al. |
| 5,399,412 A | 3/1995 | Sudall et al. |
| 5,401,267 A | 3/1995 | Couture-Dorschner et al. |
| 5,413,568 A | 5/1995 | Roach et al. |
| 5,415,643 A | 5/1995 | Kolb |
| 5,429,628 A | 7/1995 | Trinh et al. |
| 5,429,629 A | 7/1995 | Latimer et al. |
| 5,429,630 A | 7/1995 | Beal et al. |
| 5,445,628 A | 8/1995 | Gipson et al. |
| 5,447,507 A | 9/1995 | Yamamoto |
| 5,462,166 A | 10/1995 | Minton et al. |
| 5,476,457 A | 12/1995 | Roessler et al. |
| 5,487,736 A | 1/1996 | Van Phan |
| 5,489,283 A | 2/1996 | Van Tillburg |
| 5,506,035 A | 4/1996 | Van Phan et al. |
| 5,514,104 A | 5/1996 | Cole et al. |
| 5,518,801 A | 5/1996 | Chappell et al. |
| 5,520,674 A | 5/1996 | Lavon et al. |
| 5,533,991 A | 7/1996 | Kirby et al. |
| 5,542,941 A | 8/1996 | Morita |
| 5,545,156 A | 8/1996 | DiPalma et al. |
| 5,547,745 A | 8/1996 | Hansen et al. |
| 5,562,645 A | 10/1996 | Tanzer et al. |
| 5,562,650 A | 10/1996 | Everett et al. |
| 5,567,260 A | 10/1996 | McFall |
| 5,575,785 A | 11/1996 | Gryskiewicz et al. |
| 5,591,146 A | 1/1997 | Hasse |
| 5,591,148 A * | 1/1997 | McFall et al. ............... 604/378 |
| 5,591,150 A | 1/1997 | Olsen et al. |
| 5,599,339 A | 2/1997 | Horney |
| 5,601,544 A | 2/1997 | Glaug et al. |
| 5,611,790 A | 3/1997 | Osborn, III et al. |
| 5,618,282 A | 4/1997 | Schlangen |
| 5,620,430 A | 4/1997 | Bamber |
| 5,624,423 A | 4/1997 | Anjur et al. |
| 5,643,241 A * | 7/1997 | Ahr et al. ............... 604/385.01 |
| 5,649,917 A | 7/1997 | Roberts et al. |
| 5,672,248 A | 9/1997 | Wendt et al. |
| 5,692,939 A | 12/1997 | DesMarais |
| 5,693,411 A | 12/1997 | Hansen et al. |
| 5,702,378 A | 12/1997 | Widlund et al. |
| 5,704,928 A | 1/1998 | Morita et al. |
| 5,704,930 A | 1/1998 | Lavash et al. |
| 5,704,932 A | 1/1998 | Hibbard |
| 5,711,970 A | 1/1998 | Lau et al. |
| 5,720,738 A | 2/1998 | Clark |
| 5,725,821 A | 3/1998 | Gannon et al. |
| 5,746,729 A | 5/1998 | Wada et al. |
| 5,753,343 A | 5/1998 | Braun et al. |
| 5,766,213 A | 6/1998 | Hackman et al. |
| 5,769,834 A | 6/1998 | Reiter et al. |
| 5,772,967 A | 6/1998 | Wannlund et al. |
| 5,773,120 A | 6/1998 | Deka et al. |
| 5,779,860 A | 7/1998 | Hollenberg et al. |
| 5,795,921 A | 8/1998 | Dyer et al. |
| 5,800,417 A | 9/1998 | Goerg-Wood et al. |
| 5,817,079 A | 10/1998 | Bergquist et al. |
| 5,817,081 A | 10/1998 | LaVon et al. |
| 5,817,394 A | 10/1998 | Alikhan et al. |
| 5,820,616 A | 10/1998 | Horney |
| 5,824,004 A | 10/1998 | Osborn, III et al. |
| 5,846,230 A | 12/1998 | Osborn, III et al. |
| 5,851,648 A | 12/1998 | Stone et al. |
| 5,853,867 A | 12/1998 | Harada et al. |
| 5,858,011 A | 1/1999 | Brown et al. |
| 5,858,021 A | 1/1999 | Sun et al. |
| 5,865,824 A | 2/1999 | Chen et al. |
| 5,869,033 A | 2/1999 | Schulz |
| 5,874,070 A | 2/1999 | Trinh et al. |
| 5,874,071 A | 2/1999 | Yu et al. |
| 5,876,393 A | 3/1999 | Ahr et al. |
| 5,910,137 A | 6/1999 | Clark et al. |
| 5,954,705 A | 9/1999 | Sawaki et al. |
| 5,957,909 A | 9/1999 | Hammons et al. |
| 5,990,377 A | 11/1999 | Chen et al. |

FOREIGN PATENT DOCUMENTS

| | | |
|---|---|---|
| EP | 0520884 A1 | 12/1992 |
| EP | 0 117 613 B2 | 3/1993 |
| EP | 0 564 307 A1 | 10/1993 |

| | | | |
|---|---|---|---|
| EP | 0687453 A1 | 12/1995 |
| EP | 0 612 233 B1 | 4/1996 |
| EP | 0 552 345 B1 | 9/1996 |
| EP | 0 516 964 B1 | 11/1996 |
| EP | 0758543 A1 | 2/1997 |
| EP | 0768070 A1 | 4/1997 |
| EP | 0 638 303 B1 | 11/1997 |
| EP | 0804914 A1 | 11/1997 |
| EP | 0815817 A1 | 1/1998 |
| EP | 0 652 736 B1 | 10/1998 |
| EP | 0868894 A1 | 10/1998 |
| EP | 0 419 434 B2 | 11/1998 |
| EP | 0 758 220 B1 | 12/1998 |
| EP | 0 893 517 A2 | 1/1999 |
| EP | 0945110 A2 | 9/1999 |
| GB | 2168612 A | 6/1986 |
| GB | 2306333 A | 5/1997 |
| WO | WO 83/03051 A1 | 9/1983 |
| WO | WO 92/07535 A1 | 5/1992 |
| WO | WO 93/21879 A1 | 11/1993 |
| WO | WO 94/24973 A1 | 11/1994 |
| WO | WO 95/24878 A1 | 9/1995 |
| WO | WO 97/19808 A1 | 6/1997 |
| WO | WO 97/24283 A1 | 7/1997 |
| WO | WO 98/22059 A1 | 5/1998 |
| WO | WO 98/24391 A2 | 6/1998 |
| WO | WO 98/43684 A1 | 10/1998 |
| WO | WO 99/00093 A1 | 1/1999 |
| WO | WO 99/12502 A1 | 3/1999 |
| WO | WO 00/19955 A2 | 4/2000 |
| WO | WO 00/19956 A1 | 4/2000 |
| ZA | 98/4033 | 5/1998 |

OTHER PUBLICATIONS

American Society for Testing Materials (ASTM) Designation: D 3574–91, "Standard Test Methods for Flexible Cellular Materials—Slab, Bonded, and Molded Urethane Foams," pp. 303–319, published Mar. 1992.

American Society for Testing Materials (ASTM) Designation: D 4032–82, "Standard Test Method for Stiffness of Fabric by the Circular Bend Procedure," pp. 702–706, published Aug. 1982.

Federal Specification UU–T–595b, "Towel, Wiping, Paper: Industrial And Institutional," Apr. 4, 1967, 8 pages.

Federal Specification UU–T–595c, "Towel, Wiping, Paper: Industrial And Institutional," Jul. 27, 1976, 8 pages.

Gibson, P.W. et al., "Electrospun Fiber Mats: Transport Properties," AIChE Journal, vol. 45, No. 1, Jan. 1999, pp. 190–195.

Kim S.H. et al., "Synthesis and Characterization of Dextran–Based Hydrogel Prepared By Photocrosslinking," Carbohydrate Polymers, vol. 40, No. 3, Sep. 1999, pp. 183–190.

Krema, Radko et al., "What's New In Highloft Production?"Nonwovens Industry, Oct. 1997, pp. 74–78.

Lee, Seungsin et al., "Antimicrobial and Blood Repellent Finishes for Cotton and Nonwoven Fabrics Based on Chitosan and Fluoropolymers," Textile Research Journal, 69(2), Feb. 1999, pp. 104–112.

Rahn, K. et al., "New Cellulosic Polymers By Subsequent Modification of 2,3– Dialdehyde Cellulose,"Cellulose Chemistry and Technology, 32, 1998, pp. 173–183.

* cited by examiner

CENTER-FILL ABSORBENT ARTICLE WITH A CENTRAL RISING MEMBER

BACKGROUND OF THE INVENTION

To prevent leakage of body exudates from absorbent articles such as feminine care pads or napkins and disposable diapers, it is desirable that the exudates not reach the edges of the absorbent material in the article. A "center fill" strategy is desirable for leakage control, wherein fluids are preferentially held in a central region of the article. Unfortunately, in traditional absorbent articles, there is generally no means to maintain good fit of the article against the body of the wearer in use, especially once the article is wet. Though simple articles with deflection elements have been proposed, improved deflection means in cooperative relationship with multiple discrete elements of an absorbent core do not appear to be known. What is needed is an article with good center fill performance that can maintain good body fit even when the article is wet. Further, what is needed is an article with multiple absorbent elements offering excellent body fit through a three-dimensional topography that becomes more pronouncedly three-dimensional when the article is worn and compressed between the legs of the wearer while still maintaining comfort.

SUMMARY OF THE INVENTION

It has been discovered that improved body fit and leakage control can be obtained in absorbent articles by providing an absorbent core comprising two discrete absorbent members operatively associated with a central rising member. The central rising member, described more fully hereafter, is an element which deflects upwards when laterally compressed from the side. The two discrete members of the absorbent core are the central absorbent member, which serves as the primary intake member and body-contacting element, and the outer absorbent member which surrounds the central absorbent member at least along the longitudinal sides thereof. The outer absorbent member can be both wider and longer than the central absorbent member, and has a central void therein for receiving at least a portion of the central absorbent member and optionally for receiving the central rising member. The absorbent members of the absorbent core can be formed from any known absorbent material such as cellulosic fibrous webs and the like.

In the target zone of the article where fluid intake occurs, a break exists between the central absorbent member and the outer absorbent member which assists in governing effective deformation of the article when the article is compressed laterally and when the central rising member deflects upwardly. Upward deflection of the central rising member is sufficient to deflect the central absorbent member toward the body, desirably without substantially deflecting the outer absorbent member. Lateral compression of the article by the body of the user thus establishes a W-shaped cross-section of the article in the target zone as the outer sides of the outer absorbent member deflect like the outer legs of a "W" and the central absorbent member is deflected in the shape of an inverted "V" or inverted "U" to generally give an overall "W"-shape characteristic to the article, which is particularly valuable for good conformance to female anatomy. Thus, the interaction between the discrete members of the absorbent core and the central rising member during conditions of use result in an article with excellent body fit characteristics during use.

The absorbent article further comprises a topsheet and a backsheet connected to the topsheet, with the absorbent core and central rising member disposed therebetween.

The outer absorbent member typically serves as a frame or shaping element for the absorbent article and serves as a backup absorbent reservoir to receive fluid from the central absorbent member. Desirably, the outer absorbent member has a pore size greater than the pore size of the central absorbent member in the regions where the two members are likely to contact to encourage fluid to remain in the central absorbent member. Alternatively, the contact region between the two members may be treated with hydrophobic matter such as a silicone spray, impregnated wax, nonwetting fibers, or other means to reduce wicking between the two members, thus forming a wicking impediment.

The central rising member is disposed below the central absorbent member or can form part of the central absorbent member itself, being disposed therein. In use, the central rising member is capable of upwardly deflecting the absorbent material in the central absorbent member that lies above the central rising member.

Further improvements in body fit and deformation of the article in use can be achieved by adding additional features to the articles of the present invention. For example, improved deformation can also be promoted or assisted by one or more shaping lines and/or one or more crease lines in the absorbent core. A crease line lies away from the longitudinal centerline and promotes downward folding or bending of the article along the crease line (e.g., a valley fold) during lateral compression from the longitudinal sides of the article. A shaping line resides in the central absorbent member and promotes upward folding or bending (e.g., a mountain fold) during lateral compression from the longitudinal sides of the article. A shaping line coupled with at least two crease lines works to establish a W-fold geometry in the article when laterally compressed, offering good control over the upward deflection of a central absorbent member in the absorbent core. Crease lines and shaping lines, as defined therein, will be generally referred to hereafter as "bending lines."

Hence, in one aspect, the invention resides in an absorbent article having two longitudinal sides and a target zone, comprising:
  a) a liquid impervious backsheet;
  b) a liquid pervious topsheet attached to the backsheet;
  c) an absorbent core positioned between the topsheet and the backsheet, the absorbent core comprising an outer absorbent member and a central absorbent member, the outer absorbent member having a width in the target zone greater than the width of the central absorbent member in the target zone and having a central void for receiving at least a portion of the central absorbent member, the absorbent core further comprising a central rising member disposed beneath the central absorbent member, whereby lateral compression of the absorbent core from the longitudinal sides causes the central rising member to deflect the central absorbent member away from the backsheet.

In another aspect, the invention resides in an absorbent article for use on the body of a wearer, the article having two longitudinal sides and a target zone, comprising:
  a) a liquid impervious backsheet;
  b) a liquid pervious topsheet attached to the backsheet;
  c) an absorbent core positioned between the topsheet and the backsheet, the absorbent core comprising an outer absorbent member and a central absorbent member, the outer absorbent member having a width in the target zone greater than the width of the central absorbent member in the target zone and having a central void for receiving at least a portion of the central absorbent member, the absorbent core further comprising a central inflatable member disposed within the absorbent core adapted to deflect the central absorbent member away from the backsheet when activated by the wearer.

In another aspect, the invention resides in an absorbent article comprising a topsheet, a backsheet joined to the topsheet, an absorbent core disposed between the backsheet and the topsheet, the absorbent core comprising an outer absorbent member and a central absorbent member operatively associated with a central rising member, the central rising member having longitudinal sides and a longitudinally central hinge dividing the central rising member into a first portion and second portion, the article further comprising attachment means in cooperative relationship with the central rising member, wherein application of inwardly lateral compressive force to the longitudinal sides of the central rising member causes the central rising member to deflect upward along the longitudinally central hinge, and wherein the attachment means holds the central rising member in an upwardly deflected state when the inwardly lateral compressive force is relaxed.

In yet another aspect, the invention resides in a method for producing an absorbent article having a central absorbent member, the method comprising:

a) preparing an outer absorbent member, wherein the outer absorbent member has a central void;

b) disposing a central absorbent member in the central void;

c) disposing a central rising member beneath the central absorbent member;

d) disposing a backsheet beneath the central rising member and beneath the outer absorbent member;

e) disposing a topsheet above the central absorbent member and the outer absorbent member; and f) attaching the topsheet to the backsheet.

In another aspect, the invention resides in a method for producing an absorbent article comprising:

a) preparing an outer absorbent member, wherein the outer absorbent member has a central void;

b) disposing a central rising member in the central void;

c) inserting an absorbent material into the central void to form a central absorbent member.

The above method can further comprise disposing a backsheet beneath the absorbent core; disposing a topsheet above the absorbent core; and attaching a portion of the topsheet to a portion of the backsheet.

Possible uses of the present invention include absorbent articles for intake, distribution, and retention of human body fluids. Examples include feminine care pads and related catamenial devices or sanitary napkins, including "ultra-thin" pads and pantiliners and maxipads. Likewise, the present invention can be applied to diapers, disposable training pants, other disposable garments such as swimming garments, incontinence articles, bed pads, medical absorbents, wound dressings or other absorbent articles. The articles of the present invention provide significant leakage protection, fluid center-fill absorptive performance, and other desirable attributes for absorbent articles.

Definitions

"Absorbency Under Load" (AUL) is a measure of the liquid retention capacity of a material under a mechanical load. It is determined by a test which measures the amount in grams of an aqueous solution, containing 0.9 weight percent sodium chloride, a gram of a material can absorb in 1 hour under an applied load or restraining force of about 2 kPa (0.3 pound per square inch).

The AUL apparatus comprises a Demand Absorbency Tester (DAT) as described in U.S. Pat. No. 5,147,343, issued Sep. 15, 1992 to Kellenberger, herein incorporated by reference, which is similar to a GATS (Gravimetric Absorbency Test System), available from M/K Systems, Danners, Mass.

As used herein, a material is said to be "absorbent" if it can retain an amount of water equal to at least 100% of its dry weight as measured by the test for Intrinsic Absorbent Capacity given below (i.e., the material has an Intrinsic Absorbent Capacity of at about 1 or greater). Desirably, the absorbent materials used in the absorbent members of the present invention have an Intrinsic Absorbent Capacity of about 2 or greater, more specifically about 4 or greater, more specifically still about 7 or greater, and more specifically still about 10 or greater, with exemplary ranges of from about 3 to about 30 or from about 4 to about 25 or from about 12 to about 40.

As used herein, "absorbent capacity" refers to the total mass of water that a specified quantity of absorbent material can hold, and is simply the Intrinsic Absorbent Capacity multiplied by the dry mass of the absorbent material. Thus 10 g of material having an Intrinsic Absorbent Capacity of 5 has an absorbent capacity of 50 g (or about 50 ml of fluid).

As used herein, "bulk" and "density," unless otherwise specified, are based on an oven-dry mass of a sample and a thickness measurement made at a load of 0.34 kPa (0.05 psi) with a 7.62-cm (three-inch) diameter circular platen. Thickness measurements of samples are made in a TAPPI-conditioned room (50% relative humidity and 23° C.) after conditioning for at least four hours. Samples should be essentially flat and uniform under the area of the contacting platen. Bulk is expressed as volume per mass of fiber in cc/g and density is the inverse, g/cc.

As used herein, the term "cellulosic" is meant to include any material having cellulose as a major constituent, and specifically comprising at least 50 percent by weight cellulose or a cellulose derivative. Thus, the term includes cotton, typical wood pulps, nonwoody cellulosic fibers, cellulose acetate, cellulose triacetate, rayon, thermomechanical wood pulp, chemical wood pulp, debonded chemical wood pulp, milkweed, or bacterial cellulose.

As used herein, "Central Elevation" is defined as the height difference between the center of the central absorbent member along the transverse centerline of the article and the average height of the longitudinal sides of the central absorbent member along the transverse centerline of the article at the end of the Vertical Deformation Test hereinafter described. The Central Elevation for absorbent articles of the present invention can be at least about 0.5 cm, specifically at least about 1 cm, and more specifically at least about 1.2 cm and up to about 10 cm. Desirably, an absorbent article of the present invention exhibits an increase in Central Elevation in the crotch region of at least about 20%, and more specifically at least about 50%, relative to the Central Elevation in the crotch region exhibited by an essentially identical absorbent article without a shaping line.

As used herein, the "crotch region" of an absorbent article refers to the generally central region that will be in contact with the crotch of the user, near the lowermost part of the torso, and resides between the front and rear portions of the article. Typically the crotch region contains the transverse centerline of the article and generally spans approximately 7 to 10 cm in the longitudinal direction.

Many articles of the present invention are intended to be worn in the crotch of a wearer, and thus have crotch regions. However, the present invention can also be applied to other articles such as underarm pads or wound dressings where a crotch region may not exist. In such cases, the article will have a region where fluid intake is intended to occur, termed the "target region." The portion of the article including the longitudinal length of the target region and the full transverse width of the article normal to length of the target region is defined herein as the "target zone." For articles intended to be worn in the crotch, the terms "target zone" and "crotch region" are generally synonymous, whereas "target region" generally excludes the portions of the absorbent core near the longitudinal sides since the intended area for fluid intake is generally substantially central in the absorbent article.

As used herein, the term "extensible" refers to articles that can increase in at least one of their dimensions in the x-y plane by at least 10% and desirably at least 20%. The x-y plane is a plane generally parallel to the faces of the article. The term extensible includes articles that are stretchable and elastically stretchable (defined below). In the case of a sanitary napkin comprising an absorbent core, for example, the article and the absorbent core are desirably extensible both in length and width. The absorbent article, however, may only be extensible in one of these directions. Preferably, the article is extensible at least in the longitudinal direction. Examples of extensible materials and articles, and their methods of preparation, are disclosed in U.S. Pat. No. 5,611,790, issued Mar. 18, 1997 to Osborn.

As used herein, a bulk material (e.g., the absorbent components of the article or the material providing shape in the outer shaping member) is considered "flexible" if a straight, TAPPI-conditioned (50 percent relative humidity at 23° C.) strip of the material 25 cm long with a cross-section of 1 cm×1 cm can be bent 1800 around a 5-cm diameter rod without breaking and without requiring application of more than 6 Newtons of force to the ends of the strip to cause the bending over a 3-second span of time.

As used herein, the term "flexure-resistant" refers to an element which will support a bending moment, in contrast to an element which will support only axial forces. Likewise, as used herein, "flexure resistance" is a means of expressing the flexibility of a material or article and is measured according to the Circular Bend Procedure described in detail in U.S. Pat. No. 5,624,423, issued Apr. 29, 1997 to Anjur et al., herein incorporated by reference in its entirety. Flexure resistance is actually a measurement of peak bending stiffness modeled after the ASTM D4032-82 Circular Bend Procedure. The Circular Bend Procedure of Anjur et al. is a simultaneous multidirectional deformation of a material in which one face of a specimen becomes concave and the other face becomes convex. The Circular Bend Procedure gives a force value related to flexure-resistance, simultaneously averaging stiffness in all directions. For comfort, the absorbent article desirably has a flexure-resistance of less than or equal to about 1,500 grams, more specifically about 1000 grams or less, more specifically still about 700 grams or less and most specifically about 600 grams or less. For shaping performance, the central absorbent member as well as the outer absorbent member can have a flexure resistance of at least about 30 grams, more specifically at least about 50 grams, and most specifically at least about 150 grams.

As used herein, "Free Swell Capacity" (FS) is the result of a test which measures the amount in grams of an aqueous solution, containing 0.9 weight percent sodium chloride, that a gram of a material can absorb in 1 hour under negligible applied load. The test is done as described above for the AUL test, except that the 100 gm weight used in the AUL test is not placed on the sample.

The Free Swell Capacity of the materials of the present invention can be above 8, more specifically above 10, more specifically above 20, and most specifically above 30 grams/gram.

As used herein, "Free Swell:AUL Ratio" is the ratio of Free Swell Capacity to AUL. It will generally be greater than one. The higher the value, the more sensitive the material is to compressive load, meaning that the sample is less able to maintain its potential pore volume and capillary suction potential under load. Desirably, the materials of the present invention have "Free Swell:AUL Ratio" of about 4 or less, more specifically about 2 or less, more specifically still about 1.5 or less, and more specifically about 1.3 or less, with an exemplary range of from about 1.2 to about 2.5.

As used herein, "high yield pulp fibers" are those papermaking fibers of pulps produced by pulping processes providing a yield of about 65 percent or greater, more specifically about 75 percent or greater, and still more specifically from about 75 to about 95 percent. Yield is the resulting amount of processed fiber expressed as a percentage of the initial wood mass. High yield pulps include bleached chemithermomechanical pulp (BCTMP), chemithermomechanical pulp (CTMP), pressure/pressure thermomechanical pulp (PTMP), thermomechanical pulp (TMP), thermomechanical chemical pulp (TMCP), high yield sulfite pulps, and high yield Kraft pulps, all of which contain fibers having high levels of lignin.

As used herein, the term "horizontal," refers to directions in the plane of the article that are substantially parallel to the body-side surface of the article, or, equivalently, substantially normal to the vertical direction of the article, and comprises the transverse direction and the longitudinal direction of the article, as well as intermediate directions. The orientation of components in an article, unless otherwise specified, is determined as the article lies substantially flat on a horizontal surface.

As used herein, the term "hydrophobic" refers to a material having a contact angle of water in air of at least 90 degrees. In contrast, as used herein, the term "hydrophilic" refers to a material having a contact angle of water in air of less than 90 degrees.

As used herein, "Intrinsic Absorbent Capacity" refers to the amount of water that a saturated sample can hold relative to the dry weight of the sample and is reported as a dimensionless number (mass divided by mass). The test is performed according to Federal Government Specification UU-T-595b. It is made by cutting a 10.16 cm long by 10.16 cm wide (4 inch long by 4 inch wide) test sample, weighing it, and then saturating it with water for three minutes by soaking. The sample is then removed from the water and hung by one corner for 30 seconds to allow excess water to be drained off. The sample is then re-weighed, and the difference between the wet and dry weights is the water pickup of the sample expressed in grams per 10.16 cm long by 10.16 cm wide sample. The Intrinsic Absorbent Capacity value is obtained by dividing the total water pick-up by the dry weight of the sample. If the material lacks adequate integrity when wet to perform the test without sample disintegration, the test method may be modified to provide improved integrity to the sample without substantially modifying its absorbent properties. Specifically, the material may be reinforced with up to 6 lines of hot melt adhesive having a diameter of about 1 mm applied to the outer surface of the article to encircle the material with a water-resistant band. The hot melt should be applied to avoid penetration of the adhesive into the body of the material being tested. The corner on which the sample is hung in particular should be reinforced with external hot melt adhesive to increase integrity if the untreated sample cannot be hung for 30 seconds when wet.

"Papermaking fibers," as used herein, include all known cellulosic fibers or fiber mixes comprising cellulosic fibers. Fibers suitable for making the webs of this invention comprise any natural or synthetic cellulosic fibers including, but not limited to nonwoody fibers, such as cotton, abaca, kenaf, sabai grass, flax, esparto grass, straw, jute hemp, bagasse, milkweed floss fibers, and pineapple leaf fibers; and woody fibers such as those obtained from deciduous and coniferous trees, including softwood fibers, such as northern and southern softwood kraft fibers; hardwood fibers, such as eucalyptus, maple, birch, and aspen. Woody fibers can be prepared in high-yield or low-yield forms and can be pulped in any known method, including kraft, sulfite, high-yield pulping methods, and other known pulping methods. Chemically treated natural cellulosic fibers can be used such as mercerized pulps, chemically stiffened or crosslinked fibers, or sulfonated fibers. Suitable papermaking fibers can also include recycled fibers, virgin fibers, or mixes thereof.

As used herein, a "pledget" refers to an absorbent insert within an absorbent core having at least one of a width and a length smaller than the respective width and length of the absorbent core. A pledget is generally used to cause deformation or shaping of an adjoining layer of an absorbent article, and in the present invention, can be of use in shaping a pad or creating a medial hump in the pad for improved fit against the body of the wearer.

The term "sanitary napkin", as used herein, refers to an article which is worn by females adjacent to the pudendal region that is intended to absorb and contain the various exudates which are discharged from the body (e.g., blood, menses, and urine). While the present invention is shown and described in the form of a sanitary napkin, it should be understood that the present invention is also applicable to other feminine hygiene or catamenial pads such as panty liners, or other absorbent articles such as diapers or incontinence pads. The term "feminine care pad" as used herein is synonymous with sanitary napkin.

The term "stretchable", as used herein, refers to articles that are extensible when stretching forces are applied to the article and offer some resistance to stretching. The terms "elastically stretchable" or "elastically extensible" are intended to be synonymous. These terms, as used herein, mean that when in-plane stretching forces are removed, the article or absorbent fibrous structure will tend to return toward its unextended or unstretched dimensions (or original dimensions). It need not return all the way to its unstretched dimensions, however. It may return to relaxed dimensions between its unstretched dimensions and extended (or stretched dimensions).

As used herein, "thickness" of a fluff pad or other absorbent element refers to thickness measured with a platen-based thickness gauge having a diameter of 7.62 cm at a load of about 0.05 pounds per square inch (psi) [about 35 kilograms per square meter]. The thickness of the central absorbent member or the outer absorbent member or of the absorbent article in general can be from about 2 mm to about 50 mm, more specifically from about 3 mm to about 25 mm, more specifically still from about 3 mm to about 15 mm, and most specifically from about 4 mm to about 10 mm. Ultrathin articles can have a thickness less than about 6 mm.

As used herein, the term "transverse" refers to a line, axis, or direction which lies within the plane of the absorbent article and is generally perpendicular to the longitudinal direction. The z-direction is generally orthogonal to both the longitudinal and transverse centerlines. The term "lateral" refers to substantially in-plane directions having a predominately transverse component. Likewise, "inwardly lateral compression" refers to compression directed from the longitudinal sides of an article toward the longitudinal centerline thereof, applied substantially in the transverse direction.

The degree of elevation of the central absorbent member can be quantified in terms of a Vertical Deformation test. As used herein, "Vertical Deformation" refers to the height increase experienced by the body-side surface of an absorbent article when the longitudinal sides in the crotch reason are gripped and steadily moved inward toward the longitudinal axis of the article, decreasing the span between the longitudinal sides by 1.5 cm. The Vertical Deformation test apparatus comprises two clamps having a clamp width (longitudinal length of the clamped portion of the edge of the article) of 5 cm. One clamp is stationary and the other is on a track that permits the clamp to slide to increase or decrease the distance between the clamps while keeping the clamp aligned and parallel to the other clamp. The clamps should be tilted downward at an angle of 20 degrees relative to horizontal, such that both outer edges of the absorbent article are slightly elevated relative to the nearest crease line, thus somewhat simulating the positioning of the outward edges of the absorbent article that may be induced by panties with elevated elastic edges in the crotch region. The clamps are 5 cm above the surface of the track, permitting a pad to be suspended in air between the clamps, gripped in the crotch area such that a portion of the longitudinal sides of the absorbent core are held, with the clamps extending inward no more than about 3 mm from the outer edge of the absorbent core. The article should be held substantially taut in the region between the clamps without damaging the article, such that the crotch region is substantially horizontal before lateral compression begins. At a rate of about 0.5 centimeters per second (cm/s), the slidable clamp is moved smoothly toward the fixed clamp by a distance of 50% of the initial width of the article in the crotch region (or less if the article become incompressible such that more than about 5 kg of force is required to further compress the article). The height of the center of the pad or absorbent article is recorded before the clamp is moved and after the clamp is moved, yielding a difference that is reported as the Vertical Deformation. An increase in height is reported as a positive number, while a decrease is reported as a negative number. Desirably, the Vertical Deformation of the absorbent article is at least about 0.5 cm. Specifically, the Vertical Deformation is at least about 1 cm, and more specifically is at least about 1.5 cm and up to about 10 cm. Desirably, an absorbent article of the present invention exhibits an increase in Vertical Deformation in the crotch region of at least about 20%, and more specifically at least about 50%, relative to the Vertical Deformation in the crotch region exhibited by an essentially identical absorbent article without a shaping line.

As used herein, "Wet Bulk" is based on a caliper measurement of a sample according to the definition of "bulk" above (at 0.344 kPa), except that the conditioned sample is uniformly misted with deionized water until the moistened mass of the sample is approximately 250% of the dry mass of the sample (i.e., the added mass of the moisture is 150% of the dry sample weight). If the sample cannot absorb and retain enough moisture from misting to increase the mass by 150%, then the highest level of achievable moisture add-on below 150% but still above 100% moisture add on should be used. The Wet Bulk in cc/g is calculated as the thickness of the substantially planar moistened sample under a load of 0.344 kPa (0.05 psi) divided by the oven-dry sample basis weight. Absorbent materials in the absorbent members of the present invention can have a Wet Bulk of about 4 cc/g or greater, more specifically about 6 cc/g or greater, more specifically still about 10 cc/g or greater, more specifically still about 10 cc/g or greater, and most specifically about 15 cc/g or greater, with an exemplary range of from about 5 cc/g to about 20 cc/g.

DETAILED DESCRIPTION OF THE DRAWINGS

Figure 1:
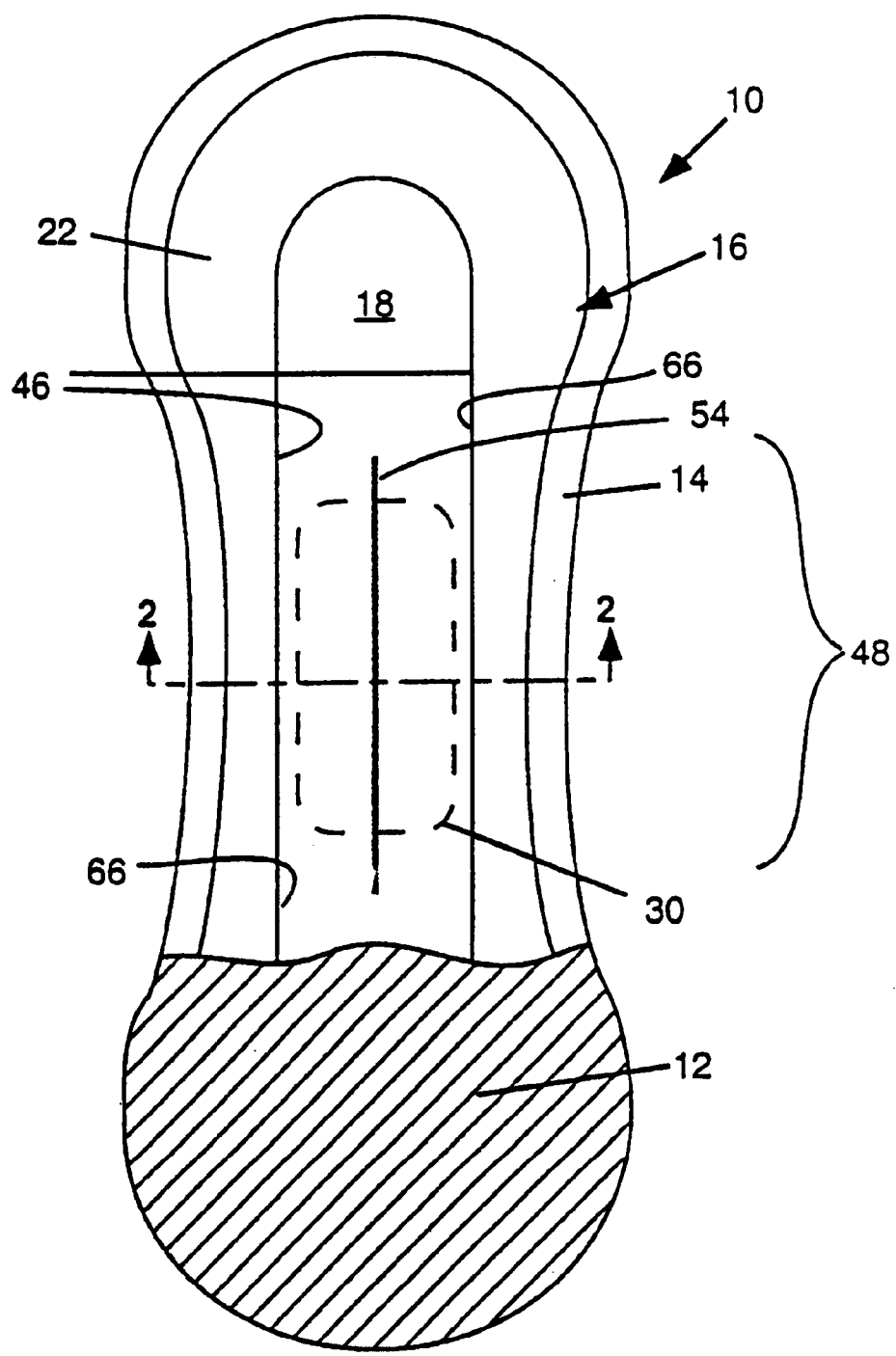
FIG. 1 depicts a top view of a sanitary napkin according to the present invention.
Figure 2:
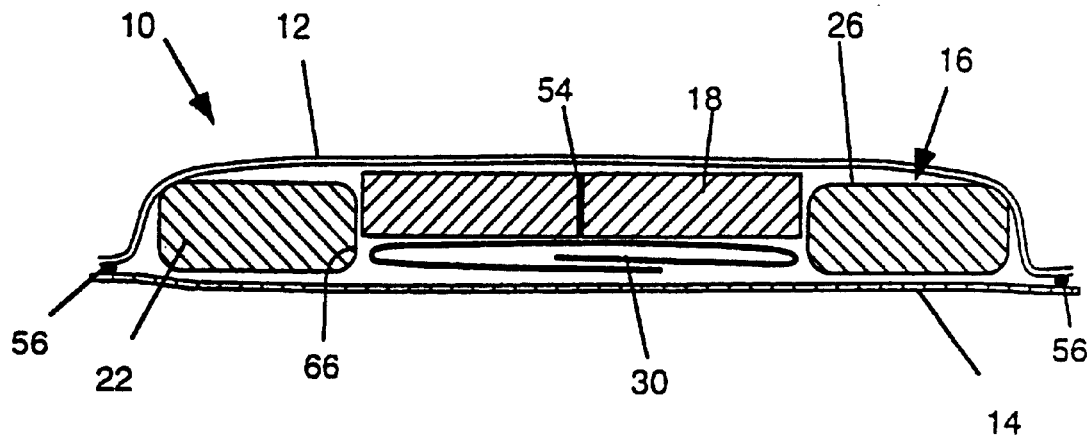
FIG. 2 depicts a cross-section of the sanitary napkin of FIG. 1.

FIG. 1 presents a top view of an absorbent article 10 according to the present invention as viewed from above, whose cross-section taken near the transverse centerline is shown in FIG. 2. The article is covered with a topsheet 12, which is cut away in FIG. 1 for to show underlying components. The topsheet 12 is connected to the backsheet 14, which is intended to be against the garments of the wearer. Between the topsheet 12 and the backsheet 14 is the absorbent core 16, which includes a central absorbent member 18 surrounded by a wider outer absorbent member 22. A central rising member 30 is disposed in the target zone 48 beneath the central absorbent member 18 and above the backsheet 14.

The central rising member 30, as depicted in FIG. 2, here is an "e"-folded section of flexible material, such as a densified airlaid web, capable of deflecting upwards when compressed from the sides. The central rising member 30 can be a flexible absorbent material such as a densified airlaid web comprising pulp fibers and thermoplastic binder particles, coform, or one or more layers of creped or uncreped tissue. Many other materials can be used to construct a central rising member. Moldable foams can be used, such as a polyethylene foam sheet creased or scored to provide bending lines therein. The central rising member 30 can also be made of various fibers, films or sheets of polymeric material, heavy-weight paper such as cardboard, or a combination or laminate of these or other materials. However, in many embodiments it is desirable that the central rising member 30 be substantially absorbent and more specifically comprise at least 50% by weight of cellulosic fibers. Other embodiments for the central rising member 30 are described below.

The central rising member 30 is disposed below the central absorbent member 18 in the target zone 48 and can act to deflect the central absorbent member 18 toward the body in response to laterally inward compression of the article 10.

The outer absorbent member 22 has a central void 66 for receiving the central absorbent member 18 and the central rising member 30. The central void 66 desirably is a region of reduced basis weight relative to the other regions of the outer absorbent member 22, but can also be a region which has been compressed in thickness substantially such that a depression is defined which can receive an absorbent insert to serve as a central absorbent member 18. As shown in the cross-section of FIG. 2, the central void 66 here passes completely through the outer absorbent member 22.

The central absorbent member 18 has an optional shaping line 54 (e.g., a slit) to help direct upward flexure of the central absorbent member 18 in the shape of an inverted "V" during lateral compression. The central absorbent member 18 can comprise between about 10% and 90% of the mass of the absorbent core 16 on a dry basis, more specifically between about 20% and 70%, more specifically still between about 20% and 60%, and most specifically from about 25% to less than 50%.

In one preferred embodiment, the central absorbent member 18 should be able to deflect upward without being substantially restrained by the outer absorbent member 22, as is the case in FIGS. 1 and 2, where the central absorbent member 18 is substantially unattached to the central absorbent member 22 apart from the common restraint offered by the backsheet 14 and topsheet 12.

The central absorbent member 18 is distinct from the outer absorbent member 22 and can be separated therefrom by a distinct gap having a width, for example, of from about 0.2 to about 2 mm in the target zone 48, to reduce the number of fibrous pathways between the central absorbent member 18 and the outer absorbent member 22. Hydrophobic matter (not shown) may also be present along the longitudinal sides 46 of the central absorbent member 18 or the sides of the central void 66 of the outer absorbent member 22 to further hinder fluid communication between the outer absorbent member 22 and central absorbent member 18. Such matter may be applied by application of melted wax, spraying of a silicone compound, coating, etc. Hydrophobic matter may be impregnated into the walls of the central void 66 or the longitudinal sides 46 of the central absorbent member 18. Such hydrophobic matter can include hot melt adhesives added to the absorbent article while molten; wax; pastes or emulsions comprising waxes;

silicone-based fluids, gels, pastes, or caulk; phenolic resins or other resins which are cured after impregnating the fibrous material of the central absorbent member or outer absorbent member; polyolefins or other plastic or hydrophobic material added as powder, particularly sintered powder, or held in place by adhesives, or by thermal bonding; and a zone of hydrophobic fibers. Either the above-mentioned gap or the hydrophobic matter or both can serve as a wicking impediment between the central absorbent member 18 and the outer absorbent member 22.

The absorbent material of either the central absorbent member 18 or the outer absorbent member 22 can comprise cellulosic airlaid webs of comminuted fibers (commonly termed "airfelt"); cellulose-superabsorbent mixtures or composites; hydroentangled webs comprising cellulosic fibers; composites of synthetic fibers and papermaking fibers such as coform, as disclosed in U.S. Pat. No. 4,879,170, issued Nov. 7, 1989 to Radwanski et al.; rayon; lyocell or other solvent-spun hydrophilic fibers, such as those disclosed in U.S. Pat. No. 5,725,821, issued Mar. 10, 1998 to Gannon et al.; cellulosic foams including regenerated cellulose foams; hydrophilic, flexible foams or absorbent foams produced from high internal phase emulsions (HIPE), such as the foams disclosed in U.S. Pat. No. 5,692,939, issued Dec. 2, 1997 to DesMarais; fiber-foam composites; the foam-structured fibrous absorbent materials of F.-J. Chen et al. disclosed in the commonly owned, copending US patent application "Fibrous Absorbent Material and Methods of Making the Same," Ser. No. 09/083,873, filed May 22, 1998; absorbent nonwoven webs; cotton; wool or keratin fibers; peat moss and other absorbent vegetable matter, and the like.

In one embodiment, at least one component of the absorbent core 16 comprises a molded, three-dimensional high bulk wet laid cellulosic web, such as an uncreped through-air dried web as taught by F.-J. Chen et al. in commonly owned U.S. patent application, Ser. No. 08/912,906, "Wet Resilient Webs and Disposable Articles Made Therewith," filed Aug. 15, 1997 or U.S. Pat. No. 5,399,412, issued to S. J. Sudall and S. A. Engel on Mar. 21, 1995. Such uncreped structures can offer a plurality of flow channels along the surface of the web. When stacked or layered with other planar materials such as a polymer film, void space can still exist adjacent the surface of the tissue web to permit rapid flow of fluid parallel to the plane of the tissue web. Further, the uncreped tissues show excellent wet resiliency and high bulk under load when wet.

Useful sources of cellulosic fibers include wood fibers, such as bleached kraft softwood or hardwood, high-yield wood fibers, and chemithermomechanical pulp fibers; bagasse; milkweed; wheat straw; kenaf; hemp; pineapple leaf fibers; or peat moss. High-yield fibers such as BCTMP can be flash-dried and compressed into dense pads which expand substantially when wetted. High-yield fiber pads that expand when wetted can be used for the absorbent cores of the present invention, as well as other expandable materials such as densified regenerated cellulose sponge materials, curled chemically stiffened cellulose fibers, and the like.

The absorbent capacity of the absorbent members can be optimized for the intended use of the article. For some uses, such as in sanitary napkins, it is desirable that the absorbent capacity of the central absorbent section 18 be at least 7 ml of fluid, specifically at least 10 ml, more specifically at least 16 ml, more specifically still at least 20 ml, and most specifically from about 15 ml to about 35 ml. In larger articles such as diapers, the absorbent capacity of the central absorbent member generally should be greater than 60 ml and can be about 300 ml or less of fluid, more specifically about 200 ml or less, more specifically still about 150 ml or less, with exemplary ranges of from about 80 ml to about 250 ml or from about 100 ml to about 300 ml.

For ultrathin pads and other absorbent articles, it is desirable that the dry components of the absorbent core 16 have a total thickness between about 2 mm and about 15 mm, and more specifically from about 3 mm to about 8 mm. When wetted, the central absorbent section 18 may increase substantially in thickness and void volume, such as a thickness increase of about 100% or greater, more specifically about 200% or greater, and more specifically still about 300% or greater. An example of a low-cost cellulosic component capable of increasing in thickness when wet is the absorbent material of Chen and Lindsay disclosed in U.S. Pat. No. 5,865,824, "Self-texturing Absorbent Structures and Absorbent Articles Made Therefrom," issued Feb. 2, 1999 to Fung-Jou Chen and J. D. Lindsay, or the densified structures of Hollenberg et al. in U.S. Pat. No. 5,779,860, "High-density Absorbent Structure," issued Jul. 14, 1998. Regenerated cellulose sponge materials are also capable of expanding significantly when wet and can be used to enhance body fit and conformability by providing the materials in nonuniform basis weights that expand in a three-dimensional shape. Densified cross-linked cellulosic mats can also be used.

Either the central absorbent member 18 or the outer absorbent member 22 or both, or individual plies thereof, may be embossed for improved control over fluid wicking, if desired. The absorbent members likewise may be apertured, slitted for improved flexibility and body conformability, perf-embossed, calendered, or pleated.

Dimensions of the components of the absorbent article 10 can be suited and optimized for particular functions. For feminine care pads, for example, the outer absorbent member 22 can have a transverse width (distance from one outer longitudinal side to the other across the transverse centerline, not the smaller edge width defined previously) of from about 4 cm to about 8 cm and a length of from about 15 cm to about 30 cm. The central void 66 in the outer absorbent member 22 may have a transverse width of from about 2 cm to about 6 cm, more specifically from about 3 cm to about 5 cm, and can have a length of from about 4 cm to about 30 cm, more specifically from about 6 cm to about 20 cm, resulting in a desirable distance from the longitudinal sides 46 of the central absorbent member 18 to the nearest outer longitudinal side of the outer absorbent member 22 (which can also be the edge width of the outer absorbent member 22, assuming no significant gap between the outer absorbent member 22 and the central absorbent member 18) of from about 0.3 cm to about 2.5 cm, and more specifically from about 0.5 cm to about 2 cm, and more specifically still from about 0.7 cm to about 1.5 cm. Appropriately larger dimensions would be desirable for diapers and many other absorbent articles. For example, the central absorbent member 18 may be from about 4 cm to about 10 cm in width in a diaper.

Basis weights of the components of the absorbent core 16 can be adjusted and optimized for particular purposes over a wide range. Generally, it is desirable that the basis weight of the central absorbent member 18 be greater than the outer absorbent member 22 because the central absorbent member 18 is intended to contain the primary source of absorbent material for the article 10, and the outer absorbent member 22 can desirably function as a secondary source of absorbent material when the absorbent capacity of the central absorbent member 18 is exceeded. Thus, the basis weight of the central absorbent member 18 can range, for example, from about 100 grams per square meter (gsm) to about 2500 gsm, more specifically from about 200 gsm to about 1200 gsm, and more specifically still from about 300 gsm to about 800 gsm. The basis weight of the outer absorbent member 22 (or, in some embodiments, of the outer shaping member) can range from about 100 gsm to about 2000 gsm, more specifically from about 200 gsm to about 1000 gsm, and most specifically from about 200 gsm to about 600 gsm.

The central absorbent member 18 generally can be of any shape such as circular, elliptical, rectangular, triangular, polygonal, dog-bone shaped, hourglass shaped, or diamond shaped, and is inset or inserted into a void 66 in the outer absorbent member 22. The central absorbent member 18 can be substantially as long as the absorbent core 16, or can have a length ranging from about 10 mm to about 170 mm. Especially in embodiments where the longitudinal ends of the central absorbent member 18 are contained within a longer outer absorbent member 22, the length of the central absorbent member 18 can be from about 20 mm to about 140 mm, more specifically from about 40 mm to about 100 mm, and most specifically from about 60 mm to about 85 mm. The maximum width of the central absorbent member 18 can be 100% of the width of the absorbent article but desirably is no more than about 90%, more specifically no more than about 75%, and more specifically still no more than about 60% of the width of the absorbent article 10. The absorbent article 10 in target zone generally can have a width of about 20 mm or greater, more specifically about 40 mm or greater, and more specifically still about 60 mm or greater.

The topsheet 12 is liquid permeable and, when the article 10 is in use, is in close proximity to the skin of the user. Desirably, the topsheet 12 is compliant, soft and nonirritating to the user's skin. It can be made from any of the conventional materials for this type of use. Nonlimiting examples of suitable materials include woven and nonwoven polyester, polypropylene, nylon, rayon or the like, particularly in the form of formed or apertured thermoplastic films, including those described in U.S. Pat. No. 4,324,246 issued to Mullane and Smith on Apr. 13, 1982 and U.S. Pat. No. 4,342,314 issued to Radel and Thompson on Aug. 3, 1982. Mechanically apertured forms can also be used. Other known cover materials can be employed, including those made from textured cellulosic basesheets with hydrophobic matter added to selected portions of the basesheet, particularly the most elevated portions of the basesheet, as described in commonly owned copending U.S. application, "Dual-zoned Absorbent Webs", Ser. No. 08/997,287, filed Dec. 22, 1997.

The outer surface of topsheet 12 can be treated with a surfactant to improve liquid penetration, and can have gradients in wettability created having different chemical treatments on the two surfaces of the topsheet, such that fluid is preferentially absorbed in targeted intake regions and repelled by other regions.

Desirably, the inner surface of the topsheet 12 is secured in contacting relation to the absorbent core 16 such as by tensional forces, by ultrasonic or thermal bonding, by needling entanglement, or by application of adhesive. One or more optional tissue layers (not shown) may be disposed directly beneath the topsheet 12 to assist in fluid intake and suitably to restrain superabsorbent particles or other particles that may be present, as exemplified by the teachings of European Patent 652,736-B1, published Oct. 28, 1998.

The backsheet 14 is generally impervious to liquids and, thus, prevents menstrual fluid or other body exudates which may be released from the absorbent core 16 from soiling the body or clothing of the user. Any backsheet material used in the art for such purposes can be utilized herein. Suitable materials are embossed or nonembossed polyethylene films and laminated tissue, desirably treated with sizing agents and wet strength agents. Breathable films that permit moisture transpiration to occur without significant condensation can also be used. The backsheet 14 may be embossed or provided with odor-controlling materials or provided with microencapsulated materials for skin wellness or release of anti-microbial or anti-odor agents upon wetting.

The backsheet 14 may also be made of a soft, cloth-like material which is hydrophobic relative to the topsheet 12. An exemplary cloth-like backsheet material is a laminate of a polyester nonwoven material and a film such as is described in U.S. Pat. No. 4,476,180 issued to Wnuk on Oct. 9, 1984. Desirably, the backsheet is a polyethylene film having a thickness of from about 0.012 mm to about 0.051 mm.

The backsheet 14 and other components may be biodegradable and/or flushable.

As shown in FIG. 2, the topsheet 12 is joined to the backsheet 14 with adhesive 56 or other connection means near the longitudinal sides of the article 10.

Figure 3:
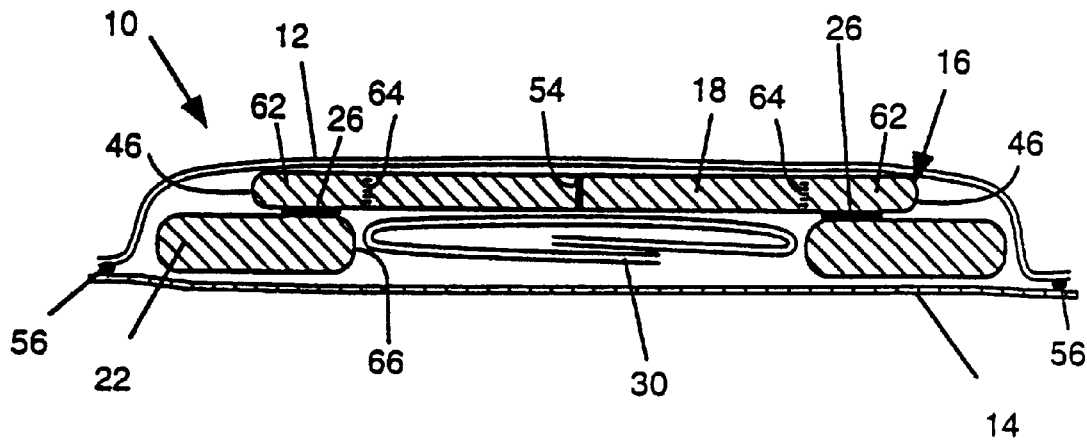
FIG. 3 depicts a cross-section of a sanitary napkin wherein the central absorbent member overlaps a portion of the outer absorbent member.

FIG. 3 depicts the cross-section of a related embodiment. In the article 10, the central rising member 30 occupies much of the space within the central void 66 within the outer absorbent member 22, such that the central absorbent member 18 does not descend to a significant degree into the central void 66. End portions 62 of the central absorbent member 18 extend past the boundary of the central void 66 and overlap the outer absorbent member 22, where they are joined thereto by adhesive sections 26, but the end portions 62 do not extend to the longitudinal sides of the outer absorbent member 22. The adhesive sections 26 desirably also impede wicking from the central absorbent member 18 to the outer absorbent member 22, as is readily achieved with a suitable application of typical hot melt or other adhesives (e.g., an add-on level of at least about 3 grams per square meter and more specifically at least about 7 gsm) to serve as a wicking impediment. The central absorbent member 18 is further provided with substantially longitudinal crease lines 64 disposed over the longitudinal sides of the central rising member 30 (or near the longitudinal walls of the central void in the outer absorbent member 22), such that the crease lines 64 naturally promote effective downward folding of the absorbent core of the article 10, while the central rising member 30 and the shaping line 54 in the central absorbent member 18 promote upward deflection of the central portion of the central absorbent member 18 during lateral compression.

In the embodiment of FIG. 3, the absorbent core 16 has a step change in thickness in the region laterally outward of the central void 66. At the longitudinal sides of the outer absorbent member 22, the absorbent material of the absorbent core 16 has a first thickness representing the thickness of the outer absorbent member 22. Moving transversely inward, the absorbent material of the absorbent core 16 experiences a step increase in thickness to a second thickness equal to the combined thickness of the outer absorbent member 22 and the central absorbent member 18. There is likewise a step change in basis weight. Moving further inward, a second step change in thickness or basis weight can be experienced upon encountering the region over the central rising member 30.

The configuration of the central absorbent member 18 overlapping a portion of the outer absorbent member 22 in FIG. 3 provides a restraint to urge the longitudinal sides of the outer absorbent member 22 back toward a horizontal orientation when inwardly lateral compressive forces are relaxed or relieved after having been flexed upwards by inwardly lateral compressive forces, such as by the legs of the user. In other words, the presence of the extended ledge of absorbent material from the end portions 62 of the central absorbent member 18 overlapping the outer absorbent member 22 helps to improve the mechanical properties of the article 10, giving it a more elastic or "springy" nature to help it adjust and conform to the body in a variety of positions without having excessive stiffness. Flexure regions are provided by the break between the central rising member 30 and the outer absorbent member 22, coupled with crease lines 64 in the overlying outer absorbent member 22, and a flexure region is also provided by the shaping line 54 in the central absorbent member 18, such that the absorbent core 16 readily conforms to the body without excessive stiffness, and such that a W-shape in the target zone 48 can be established, but the article 10 is not "dead" or devoid of elastic properties that allow the article 10 to flex back into a horizontal position when compressive forces are relaxed. The restraint offered by the extended central rising member 18 (i.e., by the longitudinal sides 46 of the central absorbent member 18 which overlap a portion of the outer absorbent member 22) plays a useful role in providing excellent elastic and other mechanical properties of the article 10 when worn.

Figure 4:
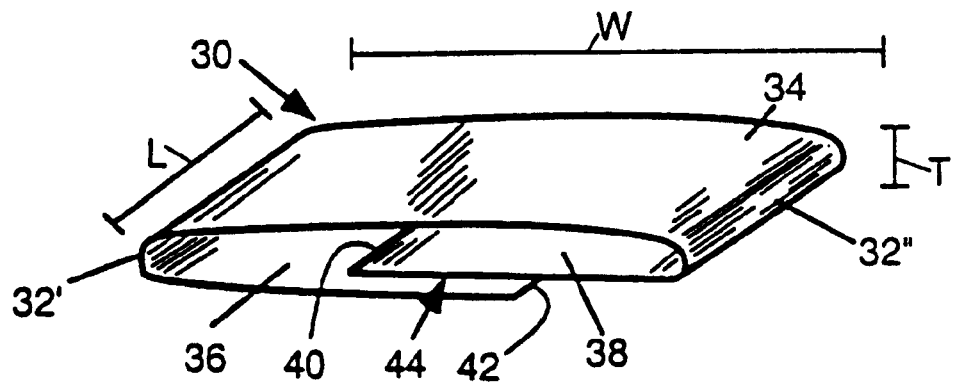
FIG. 4 depicts a an "e"-folded central rising member.

FIG. 4 depicts a perspective view of an "e"-folded central rising member 30. The central rising member 30 comprises a sheet of material that is folded or wrapped to have two longitudinal sides 32', 32", an upper portion 34, a first lower portion 36 and a second lower portion 38, each of which terminate respectively into ends 40, 42. The terminal portions of the lower portions 36, 38 overlap in an overlapping region 44. The two lower portions 36, 38 in the overlapping region 44 may be free to slide past each other or may be joined in a fixed relationship to prevent sliding of one lower portion relative to the other. In the embodiment shown, the lower portions 36, 38 are freely slidable relative to one another.

Preferably, the upper portion 34 of the "e"-folded central rising member 30 is toward the body side of the absorbent article (toward the topsheet) and the lower portions 36, 38 are toward the garment side of the article in order to obtain the best deformation of the central rising member 30 toward the body side of the user when the article is worn and compressed laterally inward.

The material forming the central rising member 30 is shown here as folded roughly into the shape of a compressed letter "e", with the lower portion 38 corresponding to the central crossbar of an "e" that extends across only a portion of the width of the "e". In other words, the folded shape of the central rising member 30 resembles a section of material folded into a tube with overlapping ends 40, 42 in an overlapping region 44, the tube being vertically compressed to be substantially flat. When laterally compressed, the lower portions of the folded material 36,38 that terminate into overlapping ends 40, 42 can mutually slide toward the opposing longitudinal side of the article. Specifically, the end 40 of the second lower portion 38 slides toward the first longitudinal side 32', while the end 42 of the first lower portion 36 may slide toward the second longitudinal side 32" or can remain substantially immobile or fixed to underlying sections of the absorbent article. During such deformation, the upper portion 34 deflects upward.

The central rising member 30 has a transverse width W, a longitudinal length L, and a z-direction thickness T. The width W of the central rising member 30 in the absorbent article prior to use can be equal to or less than the minimum width of the absorbent article in the target zone. Specifically, the width W of the central rising member can be about 90% or less, more specifically about 70% or less, more specifically still about 50% or less of the minimum width of the absorbent core in the target zone of the absorbent article. Without limitation, dimensions of width W, thickness, T, and length L for a central rising member 30 suitable for a sanitary napkin and related absorbent articles can include the following, given for the article in its unused, uncompressed state: for width W, from about 10 mm to about 60 mm, more specifically from about 15 mm to about 40 mm; for thickness T, from about 1 mm to about 15 mm, more specifically from about 3 mm to about 8 mm; for length L, from about 10 mm to about 100 mm, more specifically from about 15 mm to about 70 mm, and most specifically from about 20 mm to about 50 mm.

Figure 5:
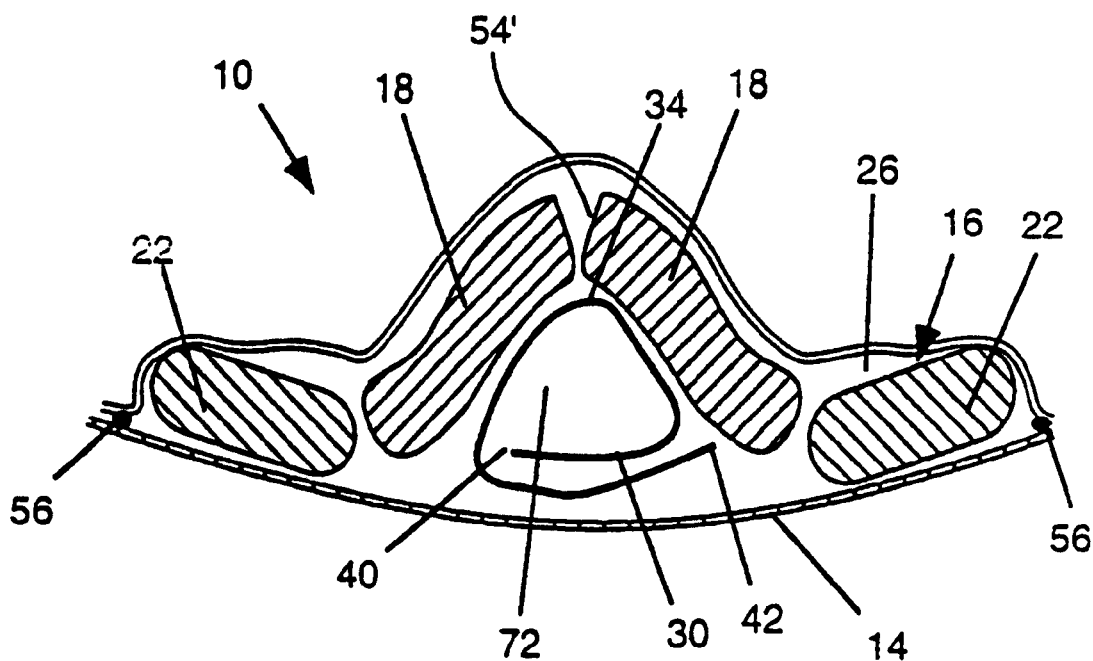
FIG. 5 depicts a cross-section of the sanitary napkin of FIGS. 1 and 3 after being subjected to lateral compression.

FIG. 5 shows the absorbent article 10 of FIGS. 1 and 2 after lateral compression, where the central rising member 30 has deflected the overlying central absorbent member 18 vertically upward. The ends 40, 42 of the central rising member 30 have moved toward the opposing longitudinal sides thereof as the upper portion 34 has deflected upward, resulting in formation of a void space 72 beneath the central absorbent member 18 and specifically within the central rising member 30.

Figure 6:
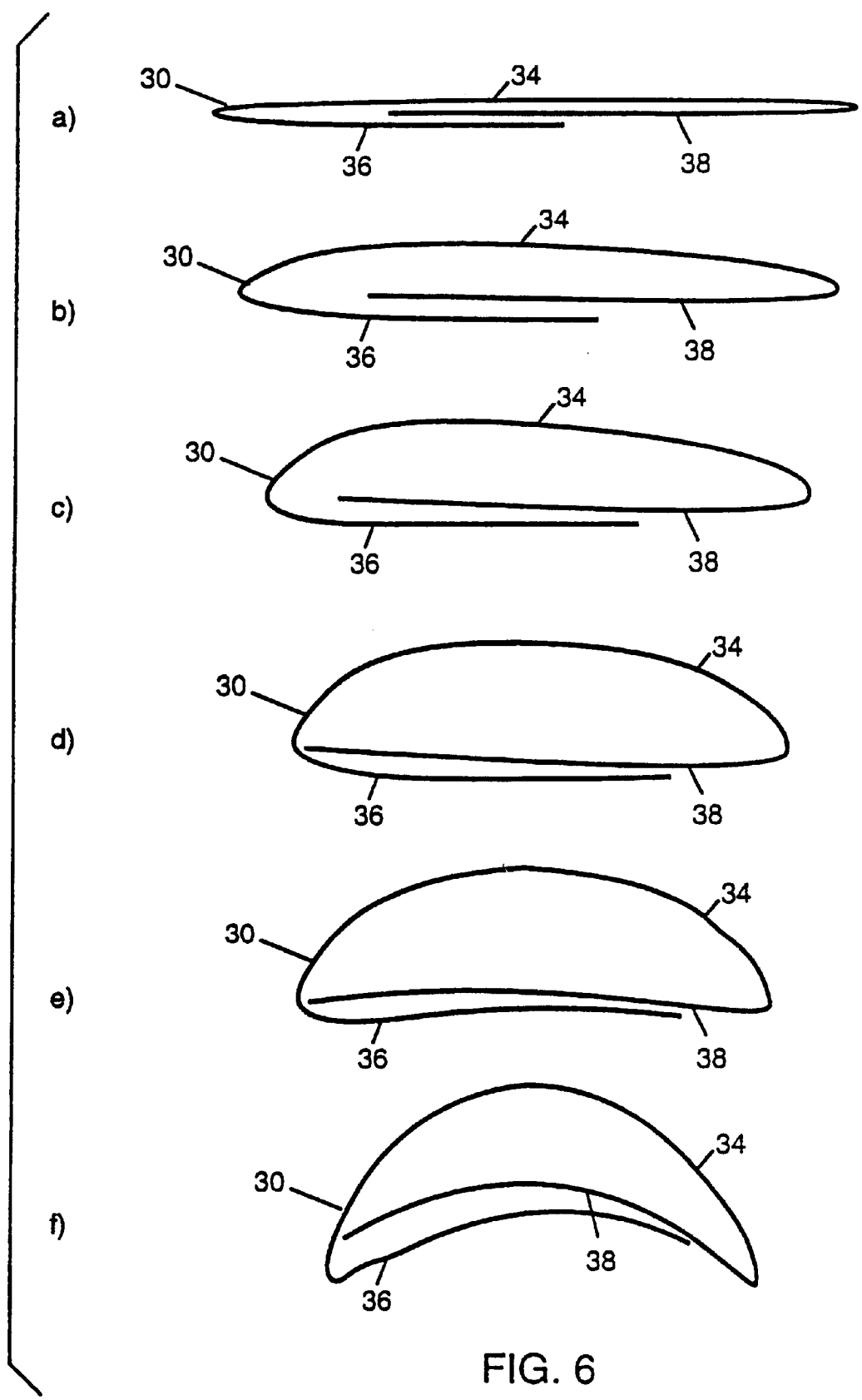
FIGS. 6A–6F depict a central rising member in various stages of lateral compression.

FIGS. 6A–6F depict a central rising member 30 in several states of deformation, beginning in FIG. 6A with a vertically compressed central rising member 30 under little or no lateral compression, with successively greater degrees of lateral compression and vertical deflection being displayed in FIGS. 6B through 6F. The central rising member 30 in FIG. 6F is sufficiently deformed laterally that even the lower portions 36, 38 of the folded material have deflected upward.

Figure 7:
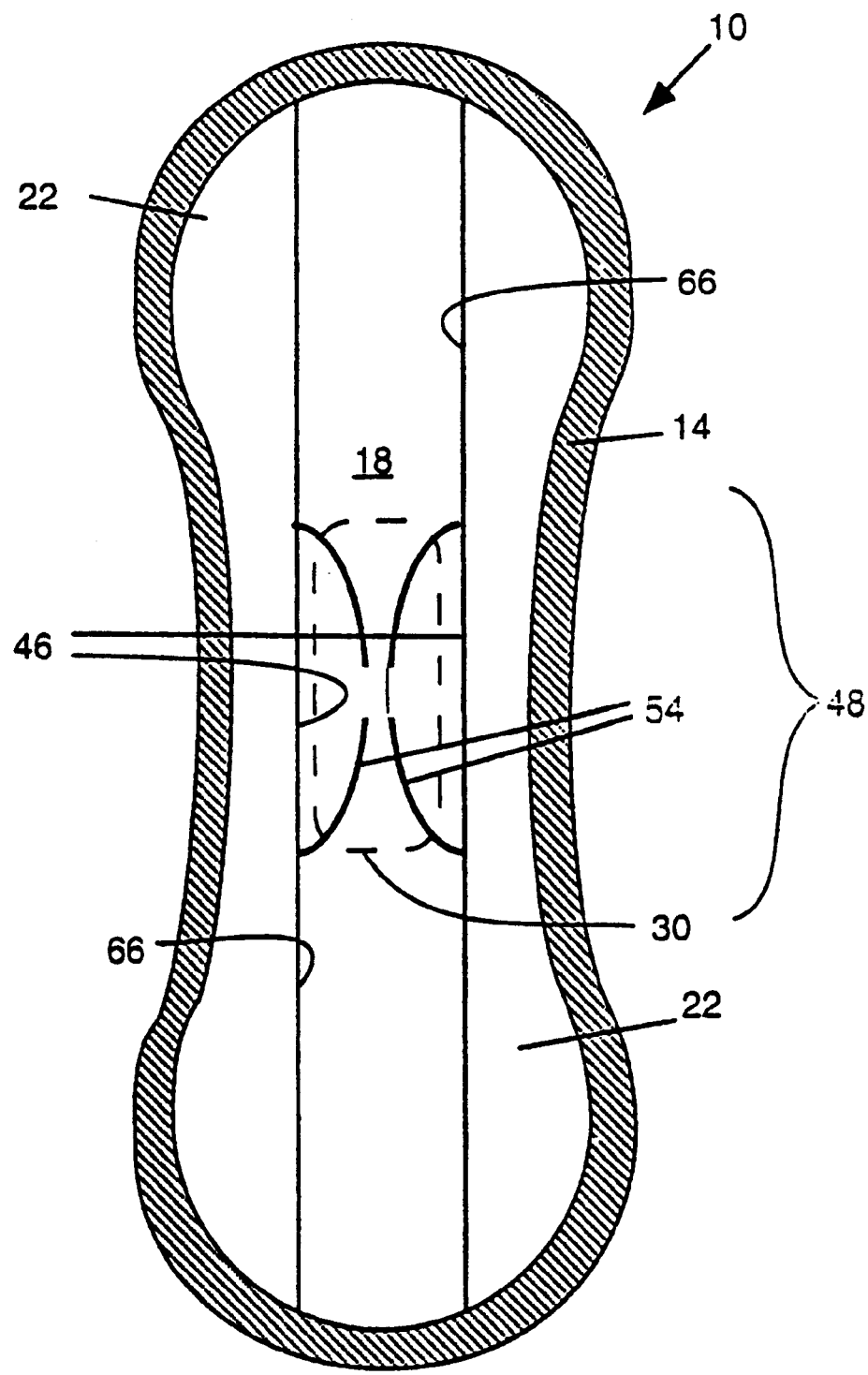
FIG. 7 depicts a top view of an absorbent article having two longitudinal strips of absorbent material forming the outer absorbent member and a longitudinal strip of absorbent material forming the central absorbent member, further having a central rising member.

FIG. 7 depicts a related embodiment of an article 10 in which the central absorbent member 18 extends across the length of the absorbent core 16 as an absorbent strip disposed between two outer longitudinal strips that form the outer absorbent member 22.

The central void 66 between the two strips of the outer absorbent member 22 receives the central absorbent member 18. A central rising member 30 is disposed beneath the central absorbent member 18. Upward deflection of the central absorbent member 30 in cooperative relationship with the central rising member 30 is further enhanced by the presence of arcuate shaping lines 54 in the central absorbent member 18 in the target zone 48. The arcuate shaping lines 54 can be slits. They allow the central portion of the central absorbent member 18 to deflect sharply upward in response to lateral compression.

Figure 8:
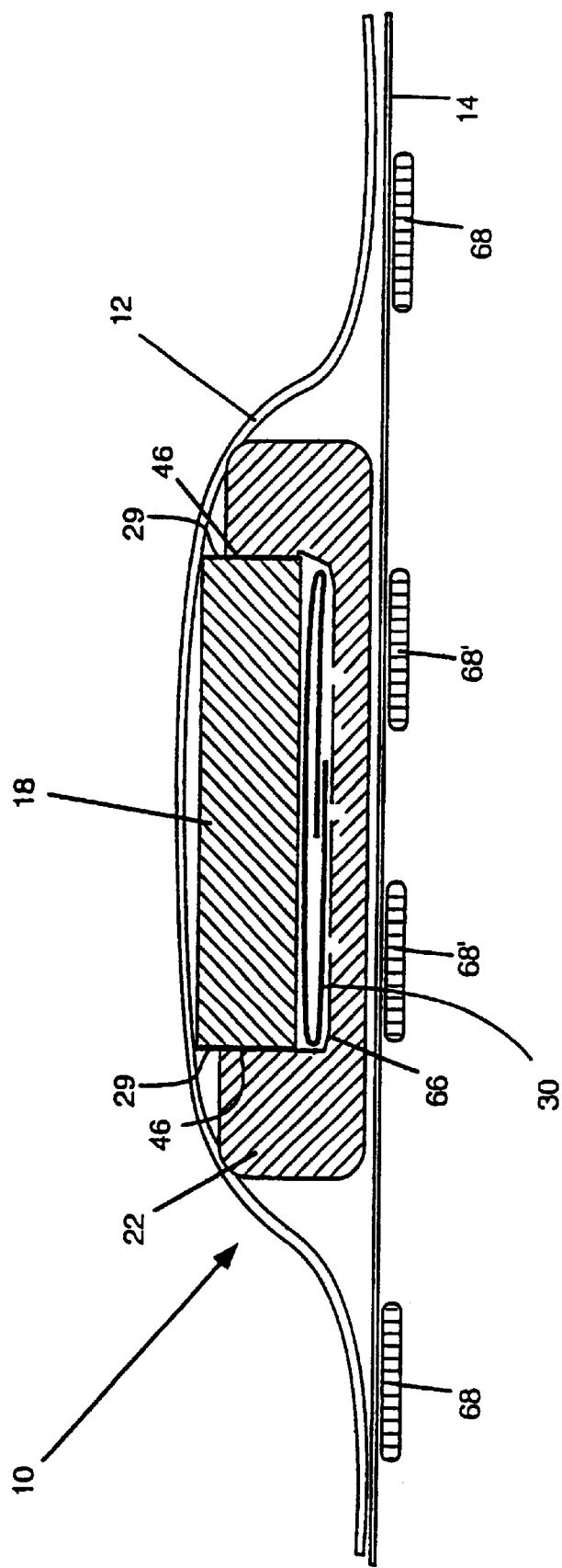
FIG. 8 depicts a sanitary napkin according to the present invention in which the outer absorbent member extends beneath the central absorbent member.

FIG. 8 depicts a transverse cross-section of a related embodiment of an absorbent article 10. The outer absorbent member 22 has a region of reduced basis weight or thickness having a surface which defines the boundary of a central void 66. Flow of fluid from the central absorbent member 18 to the outer absorbent member 22 is hindered by the presence of hydrophobic matter 29 on the longitudinal sides 46 of the central absorbent member 18, which serves as a wicking impediment.

The outer surface of backsheet 14 can be coated with adhesive such as the pressure-sensitive adhesive strips 68, 68'. The adhesive, for example, can provide a means for securing the pad in the crotch portion of a panty. Any adhesive or glue used in the art for such purposes can be used herein, with pressure sensitive adhesives being preferred. Also, before the article 10 is placed in use, the pressure sensitive adhesive should be covered with one or more removable release liners (not shown). Any commercially available release liners commonly used for such purposes can be utilized.

Figure 9:
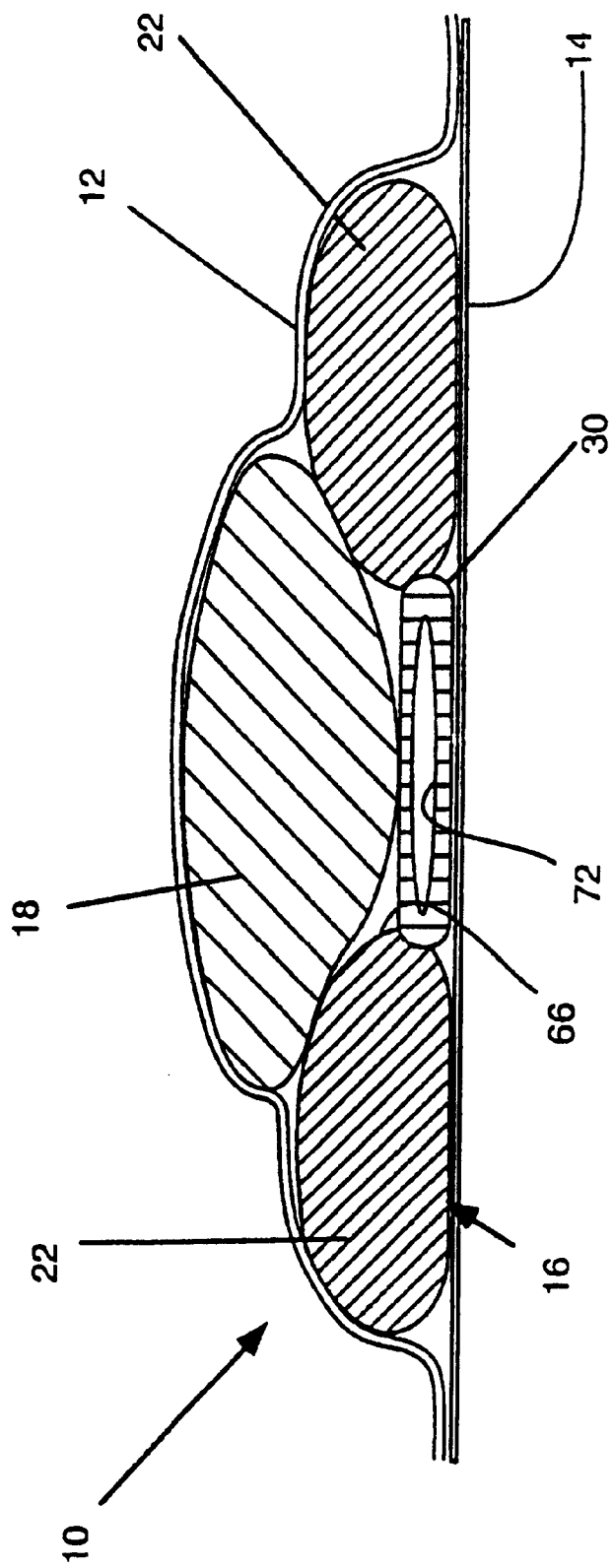
FIG. 9 depicts a cross-section of an absorbent article with tube-like central rising member.

FIG. 9 depicts a transverse cross-section of another absorbent article 10 according to the present invention. The absorbent core 16 comprises an outer absorbent member 22 which is divided into two sections along the cross-section shown to define a central void 66 which receives a central absorbent member 18. Situated within the central void 66 is a central rising member 30, depicted here in the form of a flattened tube of flexible material whose walls define an internal void space 72 which increases in size upon lateral compression by the legs of a wearer.

Figure 10A:
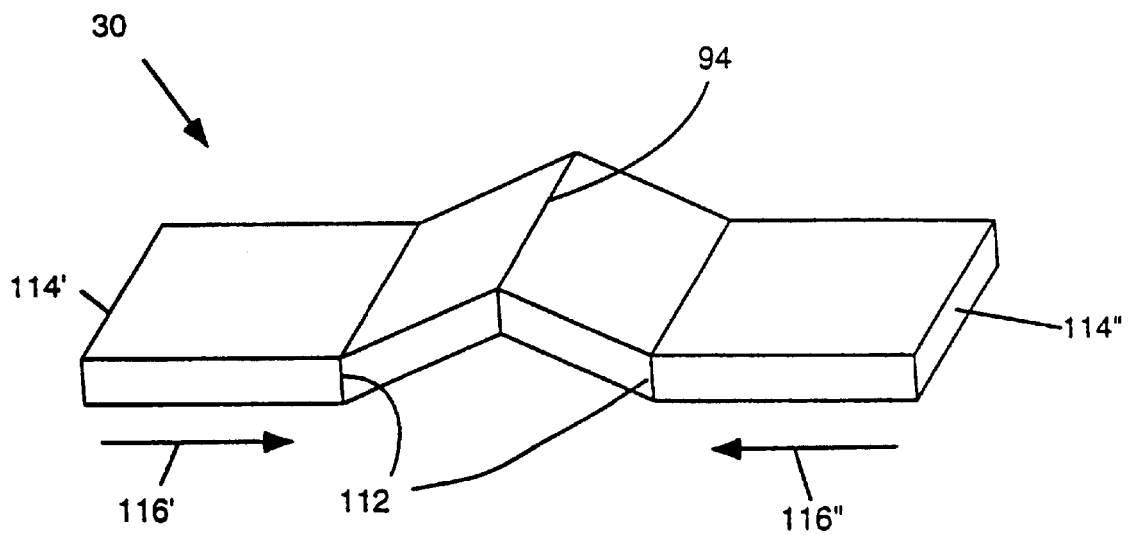
FIGS. 10A and 10B depict a perspective view of two central rising members, one that is folded or creased along its longitudinal centerline and one with a loop predisposed to deflect upward.

FIG. 10A depicts a form of a central rising member 30 comprising one or more layers of material that is folded or creased to form an inverted V-shape when the longitudinal sides thereof are moved inward toward the initial longitudinal centerline of the central rising member 30. Specifically, the central rising member 30 comprises a length of absorbent material having a central upward fold serving as a hinge 94, and two downward creases 112, such that moving the longitudinal ends 114', 114" toward each other in the respective directions indicated 116', 116" causes upward deflection along the central fold 94 to increase the apparent thickness of the central rising member 30 and deflect an overlying central absorbent member (not shown) in the vertical direction.

Figure 10B:
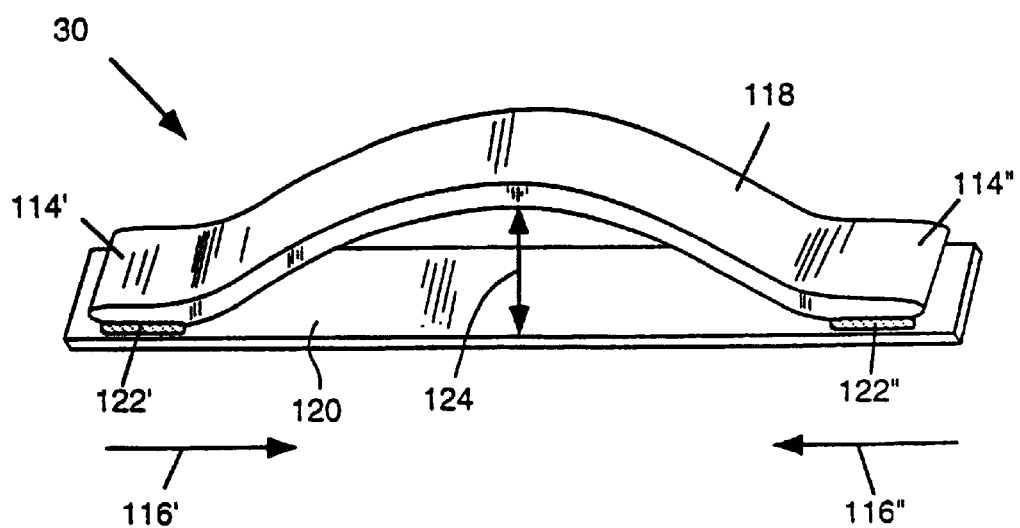

FIG. 10B depicts an embodiment of a central rising member 30 related to that of FIG. 1A, but one that is substantially free of creases or hinge elements. The central rising member 30 comprises a resilient web 118 having ends 114', 114" that are anchored to an underlying web 120 by bond areas 122', 122" which can be adhesive bonds or thermal welds and the like. The length of the resilient web 118 between the bonds areas 122', 122" is greater than the linear distance between the bond areas 122', 122", such that the resilient web 118 forms a loop that is convex toward the body side of the wearer. Prior to compression and in an unloaded state, the central rising member 30 has a gap between the central portion of the resilient web 118 and the underlying web 120 defining a distance 124 which can be about 0.5 mm or greater, and preferably less than about 5 mm, such as a gap height of about 0.7 mm to about 2 mm. When exposed to laterally inward compression, wherein the ends 114', 114" of the resilient web 118 are moved toward one another in the respective directions shown by arrows 116', 116", the gap height 124 increases and the central portion of the resilient web 118 moved vertically upward toward the body of the wearer. (As drawn, the gap height is greatly exaggerated for clarity.)

In one embodiment, the resilient web 118 comprises multiple layers of thin, flexible material such as tissue or layers of polymeric film which have been previously bent or preshaped to be predisposed to flex upward. Even with a very small gap height 124, the preshaping or prior bending of the multi-ply resilient web 118 will generally strongly promote upward flexing during lateral compression.

Figure 11:
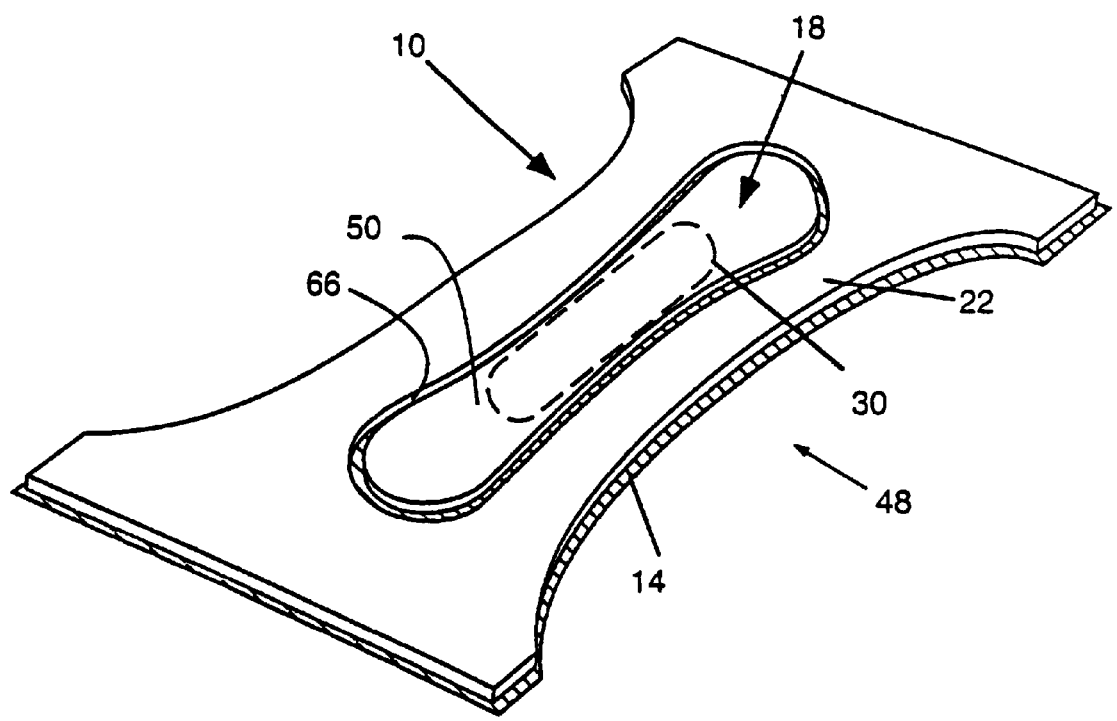
FIG. 11 shows a top view of a diaper with a central rising member beneath a central absorbent member.

FIG. 11 depicts components of an article 10 which is a diaper comprising a central absorbent member 18 having an upper layer 50 and a lower absorbent central rising member 30. A shaped outer absorbent member 22 has a central region that has been cut out, defining a void 66 for receiving the central absorbent member 18, which comprises an upper layer 50 slightly smaller in lateral dimensions than the central void 66 and substantially concentric with the walls of the void 66, and further comprises an absorbent central rising member 30. The finite gap between the sides of the upper layer 50 of the central absorbent member 18 and the sides of the central void 66 in the outer absorbent member 22 serves as a moat to impede lateral wicking from the central absorbent member 18 to the surrounding outer absorbent member 22, thus promoting center fill of the central absorbent member rather than wicking throughout the diaper. The moat can also serve to channel runoff or fast-moving liquid urine, for example, to other portions of the outer absorbent member 22 and the central absorbent member 18 to reduce leakage during an insult. While a moat can reduce wicking, it still permits easy radial spreading of bulk fluid once fluid enters the channel. Therefore, it is desirable for effective center fill performance that an additional wicking impediment be present (not shown), such as a hydrophobic matter on the outer edges of the upper layer 50 of the central absorbent member 18.

Figure 12A:
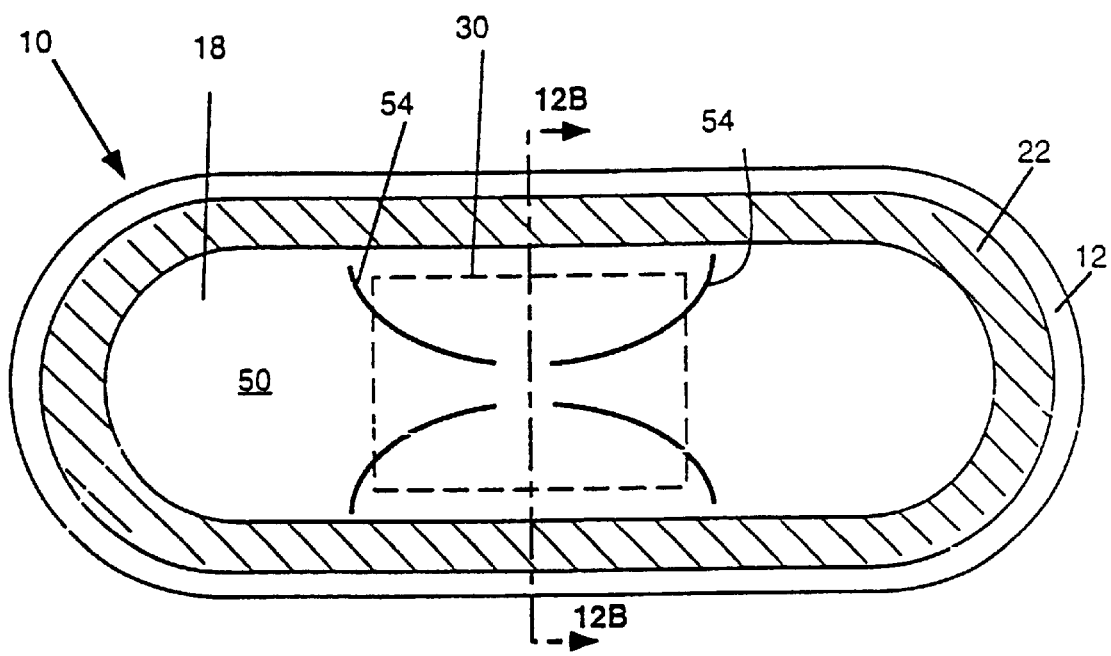
FIGS. 12A and 12B depict a top view and a cross-sectional view, respectively, of an absorbent article comprising an absorbent central rising member.
Figure 12B:
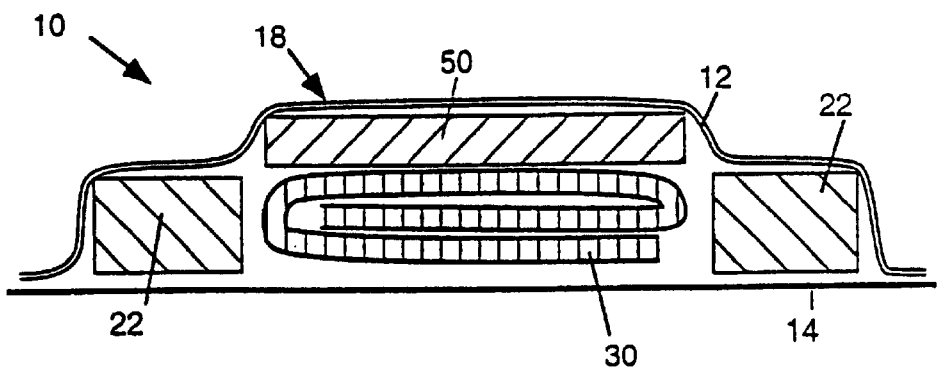
Figure 13:
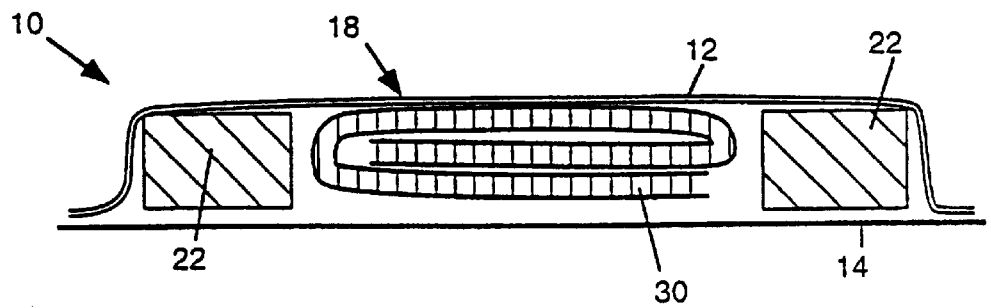
FIG. 13 depicts a cross-sectional view of an absorbent article made according to the present invention comprising an absorbent central rising member.

FIGS. 12 and 13 are discussed in the Examples below.

Without limitation, further principles for construction of absorbent articles according to the present invention are given below in terms of the specific components.

Other Embodiments for the Central Rising Member

The central rising member generally has flexure points or folded sections such as an "e"-folded web such that lateral compression from the longitudinal sides of the central rising member causes at least a portion of the central rising member to deflect upwards with sufficient force that an overlying central absorbent member can be deflected toward the body (or that the central rising member itself can rise toward the body when it serves as the central absorbent member). An absorbent central rising member can also be configured as a flattened tube or an equivalent. Other shapes can also be effective, such as a layer of absorbent material folded or held in the shape of the letter "C" rotated 90 degrees to the right, similar to an inverted "U" with the ends brought together. The rotated "C" shape is especially useful when the internal void space therein is partially filled with another section of absorbent material to prevent collapse and to help predispose the shape to flex upward during lateral compression.

By way of example, the central rising member whether fibrous or not can have a basis weight of from about 30 grams per square meter (gsm) to about 800 gsm, more specifically from about 50 gsm to about 500 gsm, more specifically still from about 50 gsm to about 300 gsm, and most specifically from about 70 gsm to about 270 gsm.

Desirably, the central rising member comprises at least one ply of a resilient material having a wall thickness wherein the resilient material defines an internal void space due to folding or layering of the material, wherein the z-direction thickness of the internal void increases in size during lateral compression as the upper surface of the central rising member is displaced upward. Alternatively, the central rising member can lack an internal void, being a single layer of material that is folded or creased to form an inverted V-shape or U-shape when the longitudinal sides thereof are moved inward toward the initial longitudinal centerline of the central rising member. An example of this construction is shown in FIG. 10A, as discussed above.

The central rising member can comprise a thermoplastic deformation element as disclosed by K. B. Buell in U.S. Pat. No. 5,300,055, issued Apr. 5, 1994, but the central rising member can also be non-thermoplastic such as a densified cellulosic web. Thus, the central rising member can have a flexure means, and particularly a longitudinally extending flexure hinge, for inducing the body facing surface of the central rising member to have a convex upward configuration when the sanitary napkin is worn. In an alternative embodiment, the deformation element has a central region having a "W" shaped cross-section wherein the body facing surface of the central rising member having the convex upward configuration is located in the central region, generally symmetrically between the longitudinal side edges of the napkin. In another embodiment, the central rising member has a cup-shaped front region and a back region having a convex upward configured body-facing surface.

Preferably, the central rising member should be resilient enough that it can lift a load of 50 grams by at least 4 mm when it is resting on a solid surface and the longitudinal sides are laterally compressed toward the longitudinal centerline of the central rising member such that the longitudinal sides thereof are brought no more than 13 mm closer due to lateral compression. Rectangular blocks 50-mm long and 5-mm square in cross section, with the 50-mm long dimension aligned with the longitudinal sides of the central rising member, can be used to evenly displace the longitudinal sides toward one another. The load to be lifted is a vertically oriented spindle and foot on a device such as a Mitutoya Digimatic Indicator (e.g., Model 543-525-1). The foot is a stiff section of acrylic plastic 0.7 mm in thickness, 50 mm long and 20 mm wide, placed over the central rising member and centered beneath the spindle of the indicator to more evenly distribute the load of the spindle. The vertical displacement caused by the lateral compression of the longitudinal sides of the central rising member is the vertical distance traveled by the spindle.

The central rising member desirably can still perform its function even when fully wetted. Thus, the central rising member desirably has a degree of wet resiliency, and specifically has a Springback of about 0.7 or greater, as defined in U.S. Pat. No. 5,672,248, issued to Wendt et al. on Sep. 30, 1997. In one related embodiment, the elastic modulus (based on machine direction tensile testing with a crosshead speed of 10 in/min, jaws 2 inches wide, and a gauge length of 2 inches) of the central rising member does not decrease by more than about 30% after being uniformly wetted for five minutes with an amount of distilled water equal to the dry mass of the central rising member, and more specifically does not decrease by more than about 20%. In another embodiment, the elastic properties of the central rising member are substantially unaffected by moisture.

In another embodiment, the central rising member can be a web or layer of resilient material, including a cellulosic densified airlaid web, which is predisposed to deflect vertically upward by virtue of a central hinge element, a shaping line, or a score mark created by creasing or folding the central rising member along its longitudinal centerline. On the garment-side surface of the central rising member, disposed on opposing sides of the longitudinal centerline (or on opposing sides of a central scoremark or shaping line), are attachment means which join together upon contact and hold the opposing sides of the central rising member together to maintain an upwardly flexed shape (e.g., a mountain fold configuration) even when the inward compressive forces that brought the opposing attachment means together are subsequently removed. Velcro® and other known mechanical attachment means can be used. The attachment means can also be magnetic wafers or buttons; adhesive materials; interlocking plastic ridges such as those used to seal resealable plastic bags, including ZIPLOC® bags; plastic or metallic snaps; and the like.

In the absorbent article of the above embodiment, the central rising member can further comprise a garment-side surface, and the attachment means can comprise a first attachment section on the garment-side surface of the first portion of the central rising member and a second attachment section on the garment-side surface of the second portion of the central rising member, wherein the first attachment section connects to the second attachment section when the garment-side surface of the first portion of the central rising member is brought into contacting relationship with the garment-side surface of the second portion of the central rising member. The attachment means can comprise a mechanical attachment means such as a hook and loop system disposed on the garment-side surface of the central rising member.

In other embodiments, the central rising member can also comprise a liquid pervious spacing structure for moving the topsheet away from the core, as disclosed by R. B. Visscher et al. in U.S. Pat. No. 5,324,278, issued Jun. 28, 1994.

The central rising member can have a flexure resistance of about 50 grams or more, more specifically about 100 grams or more, and more specifically still about 300 grams or more. Increased flexure resistance generally correlates with increased shaping ability of the central rising member, but high flexure resistance can also mean increased stiffness of the article and increased discomfort. Desirably, the flexure resistance of the central rising member is less than 1000 grams and more specifically less than 500 grams. In some cases, good performance can still be achieved when the central rising member has a relatively low flexure resistance, such as a resistance less than 100 grams, more specifically 90 grams or less, and most specifically about 80 grams or less, particularly when the central absorbent member itself is provided with bending lines and more particularly when adhesive bonds join the central absorbent member to at least one portion of the central rising member, such that the central rising member can promote upward deflection without significant stiffness and with very little risk of discomfort to the wearer.

In some embodiments, the central rising member can be wider than the central void of the outer absorbent member. For example, an absorbent article can comprise an outer absorbent member with a central elliptical hole therein. An absorbent central rising member can be disposed beneath the outer absorbent member such that a portion of the absorbent central rising member is in the hole, but side portions such as tapered sides of the central rising member can extend beyond the walls of the void and be disposed beneath the outer absorbent member.

Central Inflatable Member

Like other central rising members discussed above, a central inflatable member can urge a central absorbent member upward toward the body, but without necessarily requiring lateral compression to cause upward deflection. Thus, an inflatable bladder or envelope may be provided below or within the central absorbent member, wherein the bladder can be filled with a gas to become inflated and thus urge the central absorbent member upward. The gas may be provided by a small deformable pouch with a one-way air intake valve that can be pumped by body motion or by action of the fingers to drive air into the bladder, which also has a one-way valve or flap to hold air in the bladder but to permit its entry. The central inflatable member may also be or comprise a sealed expandable component as disclosed in U.S. Pat. No. 5,520,674, "Disposable Absorbent Article Having a Sealed Expandable Component," issued May. 28, 1996 to Lavon et al. In a preferred embodiment, the expandable component comprises a compressed resilient element disposed within an air impermeable envelope. The air impermeable envelope can be evacuated, such as by vacuum sealing, to have an internal pressure less than the outside atmospheric pressure. The expandable component expands from a first thickness to a second thickness greater than the first thickness upon opening of the air impermeable envelope.

The air impermeable envelope can comprise a port having a releasable closure. The releasable closure can be removed at the point of use of the disposable absorbent article to permit air to enter the envelope through the port, thereby providing expansion of the expandable component. In one embodiment, the releasable closure can be resealable, so that air drawn into the port does not escape when the expandable component is subjected to compressive loading.

The resilient compressed element is preferably porous, so that when a releasable closure is removed from a port in the air impermeable envelope, expansion of the resilient element draws air into the resilient element, as well as into the space in the cavity within the air impermeable envelope not occupied by the resilient element. In one such embodiment, the resilient element can comprise a porous sponge or open celled foam.

The central inflatable member can comprise an initially collapsed bladder with a one-way intake valve that can be manually expanded prior to or during use.

Space between two gas impermeable film layers or, more generally, within a bladder or gas impermeable envelope can also be filled with gas from sources other than the atmosphere. In other words, internal gas production means within the bladder or envelope can be useful for the inflation of the central inflatable member. For example, chemical means can be used to produce gas inside the bladder or envelope. Reagents such as vinegar and baking soda can be reacted to release carbon dioxide, when a barrier or seal separating the two reagents is broken or removed. Many other known gas producing agents can be used, including those that are encapsulated and yield gas only when the capsules are broken. Several related embodiments are disclosed in U.S. Pat. Nos. 3,881,491 and 3,921,232 issued to Whyte on May 6, 1975 and Nov. 25, 1975, respectively, and U.S. Pat. No. 5,876,393, issued to N. A. Ahr et al. Mar. 2, 1999.

Additional Materials in the Absorbent Core

Other components may be combined with the cellulosic materials of the absorbent core or added as separate layers or portions of the article. Such other components include odor absorbing components such as baking soda, talc powder, cyclodextrin, ethylenediamine tetra-acetic acid, zeolites, activated silica, and activated carbon granules, fabrics or fibers; superabsorbent particles and fibers; fluoropolymers; antimicrobial agents including the silver-loaded zeolites of BF Technologies, located in Beverly, Mass., sold under the trademark HEALTHSHIELD™, as well as triclosan products, chitosan or chitin derivatives (useful principles for application of chitosan finishes to nonwovenwebs and cellulosic fibers are described by S. Lee et al., "Antimicrobial and Blood Repellent Finishes for Cotton and Nonwoven Fabrics Based on Chitosan and Fluoropolymers," *Textile Research Journal,* 69(2): 104–112, February 1999); polycarboxylic acids; encapsulated perfumes; emollients such as lanolin; or skin wellness agents such as aloe vera extract (particularly aloe vera powder combined with a polyhydroxy softener) or vitamin E. Thermoplastic binder fibers may be added, with or without subsequent heat treatment for improved stability. Foam layers, foam shape-defining components, or foam particles may also be present. Plastic inserts to define shape or maintain integrity may also be used.

The absorbent cores of the present invention can comprise superabsorbent particles, such as from 5% to 90% by mass superabsorbent particles on a dry mass basis, or from about 30 to about 70% superabsorbent particles, alternatively from about 10% to about 50% superabsorbent particles and more specifically from about 10% to about 40% superabsorbent particles. Superabsorbent material can be incorporated as loose particulates, particles bound to the hydrophilic fibers, superabsorbent fibers, or as a component of the binder material or structuring composition. Superabsorbent material can also be provided in the form of a foam, as disclosed in U.S. Pat. No. 5,506,035, "Superabsorbent Polymer Foam," issued to Van Phan et al., Apr. 9, 1996, or incorporated into the void spaces of an absorbent foam.

In one embodiment, the absorbent core comprises a laminated or layered structure having superabsorbent particles or fibers present in at least one layer. The superabsorbent material can also serve as a binder to hold the fibrous composite in a densified state. For example, European Patent 758,220-B, issued to U. Widlund, Feb. 19, 1997, teaches the use of moistened superabsorbent particles to serve as a binder in creating laminated materials, with densification provided by passing the composite through a heated nip.

Superabsorbent material bonded to cellulosic fibers can also be beneficial for use in the present invention. For example, binders may be used to join the superabsorbent particles to cellulosic fibers, as disclosed by Hansen et al. in U.S. Pat. No. 5,547,745, issued Aug. 20, 1996 and U.S. Pat. No. 5,693,41 1, issued Dec. 2, 1997. (Such binder systems can also be used to attach many other solids to the fibers of the present invention, including zeolites, baking soda, activated carbon particles, $TiO_2$, clay, bentonite, talc, and the like.)

Superabsorbents can also be attached to specific portions of a cellulosic or nonwoven web, such as the elevated or depressed regions on an imprinted tissue sheet, as disclosed in U.S. Pat. No. 5,487,736 issued to D. Van Phan, Jan. 30, 1996. Fiber-superabsorbent composites can also include combinations of both anionic and cationic superabsorbent polymers, with one or both polymers joined to a substrate such as cellulose fibers via covalent bonds, and particles from the two polymer types joined by ionic bonds, as disclosed in U.S. Pat. No. 5,853,867 issued to N. Harada et al. Dec. 29, 1998. In one embodiment, discrete zones of anionic and cationic superabsorbent particles are provided in the article, such as discrete pockets alternating between cationic and anionic superabsorbent particles. Superabsorbents can also be prepared with both acidic and basic groups or anti-microbial factors to help prevent odors and bacteria growth.

Other Configurations and Additional Components

The absorbent articles of the present invention can be combined with other functional materials internally or externally (as by joining with additional layers), including but not limited to odor absorbents, activated carbon fibers and particles, baby powder, zeolites, perfumes, fire retardants, superabsorbent particles, nonwoven materials, closed cell foams, electronic devices such as alarms indicating wetness or leakage and other wetness indicators, opacifiers, fillers, aerogels, sizing agents, antimicrobial agents, enzymes, ion exchange material, or enzyme inhibitors for prevention of damage to skin, including organophilic clays for inhibition of trypsin and other proteolytic enzymes as disclosed by A. A. Schulz and K. Floyds in U.S. Pat. No. 5,869,033, "Method of Preventing Skin Irritation Caused by Fecal Enzymes," issued Feb. 9, 1999.

A variety of specific compounds can be applied for prevention or control of odors, including chelating agents and cyclodextrins, such as those of U.S. Pat. No. 5,874,070, issued Feb. 23, 1999, and U.S. Pat. No. 5,429,628, issued Jul. 4, 1995 to Trinh et al.; aryl acetoxyethanoic acid compounds, as described in U.S. Pat. No. 5,874,071, issued Feb. 23, 1999; and triethyl cytrate and zinc ricinoleate.

The topsheet and other body-contacting components can be treated with a variety of additives for odor control or for skin health and comfort, including anti-microbials, pharmaceuticals, emollients, aloe vera extract or vitamin E, and other known skin treatment compositions.

For feminine care articles, tabs and wings can be added to the sides of the article.

The entire absorbent article may comprise extensible materials, including corrugated or foreshortened absorbent materials capable of stretch in one or more in-plane directions and an extensible topsheet and backsheet. Several useful configurations for extensible articles are disclosed in U.S. Pat. No. 5,766,213, issued to Hackman et al., Jun. 16, 1998.

Optionally, a surge layer can be disposed between the topsheet and the absorbent core, specifically above the central absorbent member, to enhance intake of fluid, particularly urine and particularly in absorbent articles intended for urine management such as diapers, training pants, or incontinence pads. The surge layer is typically a high-loft nonwoven web, such as a bonded carded web, of synthetic materials such as polyethylene or polypropylene, which does not retain liquid but helps to distribute it into the underlying absorbent core. Exemplary surge layers are described in U.S. Pat. No. 5,562,650, issued Oct. 8, 1996 to Everett et al. and U.S. Pat. No. 5,429,629, issued Jul. 4, 1995 to Latimer.

Means can also be applied to reduce the tendency of a pad or sanitary napkin to bunch or fold over onto itself during transverse compression. Wings, flaps, or tabs extending from the absorbent article in the crotch region can fold over the edge of undergarments of the wearer to provide better fit, stability, and leakage protection, and can reduce undesirable bunching of the article. Wings and related structures are taught in the U.S. Pat. No. 5,267,992, "Shaped Sanitary Napkin with Flaps," issued to K. J. Van Tilburg, Dec. 7, 1993 and World Patent Application 99/00093 "Absorbent Article with Multi-Layered Extensible Wings," R. W. Patterson et al., Jan. 7, 1999.

Bending Lines

As used herein, the word "line" or "lines" in the terms "shaping line" and "crease lines" refer to narrow, elongated sections that promote folding by providing a sudden change in material properties of matter along the line relative to matter on either side of the line. A line can be straight, arcuate, sinusoidal, wavy, angular, or zig-zag-like, and can have multiple elements, such as a line that extends longitudinally followed by a bend or turn toward the center of the article, or can be a series of short segments that define a line. A shaping line or crease line may also be comprised of a series of dots, such as dots formed by adhesives or heat and pressure to create densified, bonded spots spaced apart to define a line. Lines can have a width less than about 10 millimeters (mm), desirably less than about 5 mm, more specifically less than about 3 mm, and most specifically between about 0.5 mm and about 2 mm. Since a shaping line will generally have multiple components, such as longitudinal portions and outwardly spanning segments, the terms "shaping lines" and "shaping line" can generally be used interchangeably.

During laterally inward compression from the longitudinal sides, it is desired that an essentially W-shaped fold be established in the crotch region of the absorbent article due to deflection of the absorbent core. As used herein, a "W-shaped fold" in the absorbent article means that the cross-section of the laterally compressed article along or near the transverse centerline of the article shows a shape approximated by the letter W, with outer valleys around a central mound. The central mound may be rounded, relatively flat at the top, or sharp like an inverted V. A W-shaped fold can be produced with simple lateral compression by proper placement of crease lines and a shaping line or lines. Typically, the crease lines, when used, are located outside the central absorbent member of the absorbent core of an absorbent article. Downward folding along the crease lines is typically associated with upward folding of the longitudinal sides of the article in the crotch region. The crease lines can be coupled with a shaping line or shaping lines closer to the longitudinal axis of the article than the crease lines, typically located in the central absorbent member of the absorbent core of an absorbent article, wherein the shaping line promotes or permits upward folding of the central region of the absorbent core during lateral compression to provide good body fit. The shaping line, closer to the longitudinal centerline of the article than the crease lines, is designed to translate lateral compression into vertical deflection (upward protrusion) of a central region of the absorbent article, resulting, for example, in an upward mound, particularly when combined with the downward deflection of the article along the crease lines.

Desirably, the upward mound, created near the longitudinal centerline of the article by the upward motion of the central regions of the absorbent article as directed by the shaping lines, does not persist throughout the length of the article, but, as influenced by the shaping lines, terminates just outside the crotch region to permit the article to better conform to the regions outside the crotch area, where an inverted V-shape may be useful in the rear of the article to better conform to the buttocks, and where the article generally should be relatively flat in the transverse direction and curled concave up in the longitudinal direction for best body fit in the front of the pad. Proper shaping of regions outside the crotch region during lateral compression can be achieved by providing additional slits, reinforcing elements, elastic components, or attachment elements to the absorbent core.

In one exemplary embodiment, the absorbent article comprises one or more layers of absorbent material with outwardly concave arcuate crease lines in the crotch region formed by embossing the absorbent material near the longitudinal sides of the article, further comprising a central shaping line formed by perforating or notching the absorbent material in the central region of the pad, the shaping lines having a geometry similar to a double headed arrow with reverse arrow heads, or "> . . <", centered along the longitudinal centerline of the article between the crease lines, and with the longitudinal axis of the arrow aligned with the longitudinal axis of the article. Such a geometry for the shaping line permits the central region of the absorbent core between the outward "arrow heads" to deflect upward while downward deflection occurs along the crease lines. Another successful geometry for the shaping line is a pair of outwardly concave arcuate lines whose midpoints touch or approach each other, longitudinally aligned and substantially symmetrically placed about both sides of the longitudinal axis in the crotch region between the outer crease lines, and desirably smaller in length than the crease lines. Such arcuate crease lines resemble the shape of a right and left parentheses placed back to back, or ")(", with the vertical axis of the parentheses substantially aligned with the longitudinal axis of the article. Likewise, the shaping line in many embodiments can be described as convex toward the longitudinal centerline of the article and generally contained within the absorbent core and specifically generally contained within the central absorbent member.

The shaping line or crease lines of the absorbent article can generally be created in any way likely to guide the folding of a flexible material having a degree of intrinsic stiffness such as an air laid pad, a mat of fluff pulp, a stack of tissue layers, a web of coform material or other fiber-polymer composites, or a high-loft nonwoven web. The shaping line or crease lines desirably are produced by one of more treatment methods such as embossing, stamping, or other known methods for creating densified regions, as described in U.S. Pat. No. 4,655,759, issued Apr. 7, 1987 to A. Y. Romans-Hess et al. Other methods for line formation include slitting; slotting; cutting; notching; tearing; thermobonding (application of heat to create bonding, particularly with thermoplastic materials or heat-setting resins); hot pressing (simultaneous application of heat and pressure, especially in conjunction with thermoplastic binder materials, thermosetting plastics, or heat setting resins); ultrasonic bonding; perforating; perf-embossing; needling; impregnation by resins, waxes, or thermoplastics; hydraulic cutting by water jets or other fluid jets; pre-folding; creasing; scoring; or removing material by abrasion, ablation, picking, scraping, or suction.

Crease lines and shaping lines can also be created by bonding a portion of the cover or backsheet to a compressed portion of the absorbent material using the methods described by Mogor in U.S. Pat. No. 3,575,174, issued Apr. 20, 1971. The articles of the present invention can also comprise embossments in the back region of the article to promote an inverted V-shape fold in the rear of the article for more comfortable article placement between the buttocks of a user.

The length spanned by the shaping line or lines in the longitudinal direction can be at least about 1 cm, specifically at least about 2 cm, more specifically from about 3 cm to about 10 cm, more specifically still from about 4 cm to about 8 cm, and most specifically from about 4 cm to about 6 cm. In sanitary napkins and other absorbent articles, a longitudinal slit or notch, if present, desirably can be from about 4 cm to about 6 cm long. The longitudinal length of the crease lines can be smaller than that of the shaping lines, but in most embodiments desirably is about the same as or longer than that of the shaping line. For example, the crease lines can be longer than the shaping lines in the longitudinal direction by at least about 1 cm, more specifically at least about 2 cm, more specifically at least about 3 cm, and most specifically from about 2.5 cm to 5 cm.

Methods of Making

Generally, automated equipment can be used similar to the production lines already used for production of sanitary napkins, diapers, and the like, with minor modifications to produce the present invention. Modular systems are especially preferred, wherein the various unit operations in the production line can be moved and replaced with other modules without necessitating a complete rebuild of a machine. Examples of useful machines and methods of using them for the production of absorbent articles are disclosed in U.S. Pat. Nos. 4,480,516 and 5,567,260.

The production line can include a hammermill for production of comminuted fibers, if fluff pulp is to be used, or absorbent material in roll form can be provided, including airlaid webs, coform, mechanically softened pulp sheets, tissue webs, and the like. Likewise, the nonwoven or film components of the absorbent article are also generally provided in roll form. Roll goods are unwound and cut to shape, using methods such as die cutting, slitters, or water jets, and the components placed in proper relationship one to another, typically with online bonding at selected regions provided by spray adhesive, contact with ultrasonic horns or heated embossing elements, or other bonding means known in the art. Components may be moved on continuous belts from one operation to another, and may be further transported with vacuum pick up shoes, jets of air, mechanical pincers, and the like.

For example, a web of airlaid material, coform, or a microstrained pulp sheet of width suitable for the absorbent core of an absorbent article may be unwound and slit into three strips, the middle strip desirably being wider than either of the two side strips. Alternatively, strips from three rolls of absorbent material may be unwound and brought into proximity to each other, with the central strip having different material properties than the other strips, and preferably having edges pre-treated with hydrophobic matter to serve as wicking impediment. For example, a role of absorbent material may easily be coated or painted on the sides with hydrophobic matter such as silicone water repellant materials or wax, such that the wicking impediment is already present on the central absorbent member before it is unwound.

The three absorbent strips are directed in the same direction, the machine direction, with two side strips spaced apart by a width approximately equal to or less than the width of the middle strip. A backsheet layer meanwhile is unwound from a roll and cut to the desired shape and a central rising member is placed thereon, preferably with adhesive attachment. The central strip optionally is provide with slits or embossments to serve as a shaping line. At this point, adhesive may be applied to the edges of the central strip to serve as an impediment and to hold the strip in place by connection to the backsheet or to the outer strips, onto which the central absorbent member may overlap. The strips are cut to length, disposed on the backsheet with a central rising member beneath the central strip, and a topsheet is then placed over the absorbent core and attached to the backsheet.

Alternatively, a central rising member such as a cut section of an "e"-folded web may be attached at periodic, spaced apart intervals to the garment-side surface of the central strip of absorbent material before it is joined to the backsheet.

Wings, adhesive tape strips, mechanical fasteners, cuffs, and the like may also be added using methods known in the art.

In one embodiment, an absorbent article according to the present invention can be created by placing a central rising member into a void in an outer absorbent member, followed by insertion of a central absorbent member. The void can be formed by airlaying materials over a template with variable permeability to cause lower basis weight in a central portion, or it can be created by mechanically compressing the central portion of an absorbent layer, or by mechanically removing absorbent material therefrom.

For example, a depression or stamped out region can be formed in an absorbent pad, whereafter an "e"-folded or "c"-folded coform web or flattened rubber tubular central rising member is placed in the void and a central absorbent strip such as an airlaid web is placed in the depression or stamped out region to serve as a central absorbent member.

Related embodiments can be produced by simply stamping out the region of the absorbent core in a central region to define an outer absorbent member with a void therein. A relatively flat central rising member is placed in the void, and then a central absorbent member such as a mat of fluff pulp is placed over the central rising member. The absorbent core thus formed is attached to a backsheet and a topsheet is further joined to the article, either by fine adhesive spray over portions of the outer absorbent member and central absorbent member, and/or by adhesive connection to the backsheet along the periphery of the article.

High speed, automated equipment can be used to perform the manufacture of the article. A central absorbent member surrounded on all sides by an outer absorbent member generally must be placed into a central void with precision and good registration, which can be challenging at high speeds but still feasible. However, for ease of manufacture and reduced cost, the central absorbent member is an elongated strip that extends substantially the length of the article and is bound by the outer absorbent member only along the longitudinal sides of the central absorbent member, which sides desirably are substantially straight and parallel. In this case the central absorbent member can be a continuous strip which need only be registered laterally and cut at the ends to place it properly in the central void between an outer absorbent member comprising two discrete portions. In one embodiment, the outer absorbent member and central absorbent member are cut from a single strip of absorbent material, with the central portion (the central absorbent member) being momentarily lifted during manufacture to permit insertion of a central rising member therebeneath. However, the central rising member can be centered appropriately on an adhesive-coated backsheet before attachment to the absorbent members of the article, followed by addition of the topsheet, to provide an article within the scope of the present invention.

Several methods can be applied for attaching hydrophobic fibers or other hydrophobic matter to the sides of a central void in the outer absorbent member or to the longitudinal sides of the central absorbent member to form an optional wicking impediment. Hydrophobic fibers may be placed in discrete areas of an absorbent core as taught in U.S. Pat. No. 5,817,079, "Selective Placement of Absorbent Product Materials in Sanitary Napkins and the Like," issued to R. Bergquist et al., Oct. 6, 1998. A related approach which can be applied to the present invention is given by Csillag in U.S. Pat. No. 4,015,604, issued Apr. 5, 1977. An absorbent product is disclosed with side leakage control means comprising a narrow longitudinally extending zone along each side edge of the product but spaced away from each of the side edges. This zone is impregnated with a liquid hydrophobic material from the garment facing surface to the body facing surface of the product. The hydrophobic impregnate is applied to a hydrophilic pad as the pad passes through the manufacturing equipment. Likewise, Canadian Patent No. 884,608 issued to Levesque, Nov. 2, 1971, relates to treating the edges of a sanitary napkin product with hydrophobic material in order to prevent side leakage. In accordance with Levesque, the absorbent layer in the zone of the edges of the absorbent material is rendered hydrophobic while being maintained in a gas and moisture vapor permeable condition. The hydrophobic zone may be coated with a liquid repellent composition or chemically modified to render the fibers hydrophobic.

EXAMPLES

Several examples of absorbent articles were made with the materials listed in Table 1 below:

TABLE 1

Basic materials used in construction of absorbent articles for the Examples.

| Component | Manufacturer | Description |
| --- | --- | --- |
| Topsheet | | |
| Spunbond material | Kimberly-Clark Corp. | 0.6 osy polypropylene spunbond web, "Delta" version, treated with 0.3% add-on of surfactant (described below), pin apertured |
| Surfactant treatment | ICI Americas, Inc. | 45% (w) polyethoxlated hydrogenated ethoxylated castor oil; 55% (w) sorbitan monooleate |
| Adhesive | National Starch and Chemical Co. | NS-34-5610: slot-coated, pinstripe pattern, applied at a level of about 5 gsm or less. |
| Fluff | Kimberly-Clark Corp. | Coosa River CR54 debonded softwood pulp comminuted with a hammermill |
| Densified airlaid webs | | |
| Completed web | Concert Fabrication, Ltee | 90% softwood fibers and 10% binder fibers with overall densities of 0.1–0.2 g/cc. |
| Fibers | Weyerhaeuser Co. | NB-416: bleached southern softwood kraft |
| Binder fibers | Hoechst Celanese Corp. (Trevira Company) | Celbond #255: PET core, activated co-polyethylene sheath, 50/50 core/sheath ratio, concentric, 2.8 dpf, with T-255 fiber finish |
| Coform | Kimberly-Clark Corp. | 70% bleached kraft southern softwood, 30% polyethylene, basis weight of 228 gsm |
| Backsheet | | |
| Polyolefin film | Edison Plastics Co. | A low density polyethylene, 20 gsm, rose color, 2 mil gauge after embossed with pattern MFST (male fine square taffeta), coated with contact adhesive on one side |
| Adhesive | National Starch and Chemical Co. | NS-34-5610, less than 15 gsm added, slot-coated, pinstripe pattern |
| Garment adhesive | National Starch and Chemical Co. | NS-34-5602, less than 45 gsm applied, slot coated, two 15 mm side lines of adhesive with 19 mm space between them |
| Release paper | Akrosil Inc. | White base sheet, one side coated with silicone release agent, other side printed |

EXAMPLES 1–3

Examples 1 through 3 were made generally according to FIGS. 12A and 12B, with exceptions noted below, and with the materials described in Table 1 unless otherwise noted.

In Example 1, the central absorbent member comprised a layer of a 250 gsm densified airlaid web with a density of 0.14 g/cc. The outer absorbent member was a densified airlaid web with a basis weight of 175 gsm and a density of 0.1 g/cc.

A central longitudinal slit 100 mm in length was made manually with a rotary blade knife in the central absorbent member.

The central rising member 30 beneath the central absorbent member 18 was a section of densified airlaid web with a basis weight of 175 gsm and a density of 0.1 g/cc, cut to dimensions of 110 mm by 70 mm and folded with two creases normal to the long direction and evenly spaced apart to yield an "e"-folded web with a width of about 40 mm and a length of 70 mm. The creases defining the folds were oriented in the longitudinal direction of the article so that the e-fold shape of the central rising member would be evident in a transverse cross-section, such as is shown in FIG. 12B.

The final pad was 238 mm long and 86 mm wide. The outer absorbent member 22 had external dimensions of 218 mm in length and 65 mm in width. The central absorbent member 18 was 196 mm long and 43 mm wide.

The arcuate slits forming the shaping line 54 in the upper layer of the central absorbent member 18 were 74 mm long and were substantially as shown in FIG. 12A. The spunbond topsheet 12 with floral pin aperturing (0.081 inch pins spaced about 0.4 mm apart in a continuous pattern over the full length of the pad but only in the central 38 mm of the transverse width) was held in place by light adhesive. Likewise, adhesive joined the backsheet 14 to overlying components. The backsheet 14 was provided with adhesive strips and release paper (not shown in FIG. 12) for attachment to the garment. The garment-contacting adhesive was provided in two 15-mm wide, 190-mm long longitudinal strips, leaving the central 19 mm wide region about the longitudinal centerline free of adhesive. In the crotch region, the width of the adhesive was extended outward an additional 10 mm toward the outer longitudinal sides (reaching the region directly underneath the outer longitudinal sides of the outer absorbent member) such that a 190 mm long rectangular section of adhesive on either side of the longitudinal centerline had a width of 25 mm, still leaving the central 19 mm free of adhesive. The placement of adhesive bands was intended to promote better control of deformation of the pad 10 in use to better establish a W-fold geometry.

When the resulting pad 10 was grasped along the longitudinal sides in the crotch region and laterally compressed, the central absorbent member 18 deflected upward in the crotch region, indicating the potential for good body fit in use. The overall shape of the deformed pad in a transverse cross-section was roughly W-shaped. Vertical deflection in the central portion of the pad was enhanced relative to a similar pad made without the central rising member 30.

Examples 2 and 3 were generally made according to Example 1, except that the outer rim of the pad was trimmed along the longitudinal sides to give the pad an overall width of 71 mm. In Example 2, the central absorbent member was a densified airlaid web with a basis weight of 175 gsm instead of the 250 gsm web of Example 1. The density of the central absorbent member was 0.1 g/cc. The central rising member was an "e"-folded web of a densified airlaid web having a density of 0.14 g/cc. In the "e"-folded central rising member, approximately 1 cm space was provided between the terminal ends (40 and 42 in FIG. 4) of the central rising member and the respective opposing longitudinal sides (32' and 32", respectively, in FIG. 4), providing space for significant lateral sliding of the lower portions (36 and 38 in FIG. 4) of the central rising member during lateral compression, and resulting in an e-folded cross-section better characterized by that of the central rising member 30 in FIG. 4 than that of FIG. 12B.

In Example 3, 228-gsm coform was used for the outer absorbent member, the central absorbent member, and the central rising member, which was folded as in Example 2. The longitudinal ends of the central rising member were rounded to have a radius of curvature at the 4 corners of the folded central rising member of about 1 cm.

As with Example 2 and 3, good upward deflection of the central rising member was observed during lateral compression of the article from the longitudinal sides. The additional space between the terminal ends and the longitudinal sides of the central rising member promoted somewhat greater upward deflection in Examples 2 and 3 than in Example 1.

EXAMPLE 4

Example 4 is a hypothetical example according to Example 1, except that the upper layer 50 of FIG. 12B is removed, leaving the "e"-folded absorbent central rising member 30 as the primary component of the central absorbent member 18, as shown in FIG. 13. Thus, the central absorbent member 18 is folded web comprising an absorbent central rising member 30 and, in fact, consists essentially of the absorbent central rising member 30.

It will be appreciated that the foregoing examples, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

We claim:

1. An absorbent article having a first end, a second end, two generally longitudinal sides, a top surface, a bottom surface, a thickness and a target zone, the absorbent article comprising:
   a) a liquid impervious backsheet;
   b) a liquid pervious topsheet attached to the backsheet;
   c) an absorbent core positioned between the topsheet and the backsheet, the absorbent core comprising:
      a central absorbent member having a width in the target zone;
      an outer absorbent member defining a central void open toward the top surface of the absorbent article for receiving at least a portion of the central absorbent member; the outer absorbent member having a width in the target zone greater than the width of the central absorbent member in the target zone; and
      a central rising member disposed beneath the central absorbent member, adapted to deflect the central absorbent member away from the backsheet upon application of compression forces laterally to the generally longitudinal side of the absorbent article.

2. The absorbent article of claim 1, further comprising a wicking impediment between the outer absorbent member and central absorbent member.

3. The absorbent article of claim 2, wherein the wicking impediment comprises hydrophobic matter.

4. The absorbent article of claim 2, wherein the wicking impediment comprises an adhesive.

5. The absorbent article of claim 2, wherein the wicking impediment comprises liquid impervious matter.

6. The absorbent article of claim 2, wherein the wicking impediment comprises a gap.

7. The absorbent article of claim 2, wherein the wicking impediment comprises hydrophobic matter lining at least a portion of the central void in the outer absorbent member.

8. The absorbent article of claim 1, wherein the central absorbent member overlaps a portion of the outer absorbent member.

9. The absorbent article of claim 1, the central absorbent member overlaps the outer absorbent member in the target zone.

10. The absorbent article of claim 1, wherein the central rising member is disposed within the central absorbent member.

11. The absorbent article of claim 1, wherein the central absorbent member is a folded web.

12. The absorbent article of claim 1, wherein the central rising member has a dry mass and the central rising member experiences a decrease in elastic modulus of no more than about 30% when uniformly wetted with an amount of distilled water equal to the dry mass of the central rising member.

13. The absorbent article of claim 1, wherein the central rising member is absorbent.

14. The absorbent article of claim 1, wherein the central rising member comprises a fibrous mat.

15. The absorbent article of claim 1, wherein the central rising member is the central absorbent member.

16. The absorbent article of claim 1, wherein the central rising member is not absorbent.

17. The absorbent article of claim 1, wherein the central rising member prior to lateral compression has a thickness of about 5 mm or less.

18. The absorbent article of claim 1, wherein the central absorbent member comprises an upper layer and a lower layer, the upper layer being wider than the lower layer.

19. The absorbent article of claim 1, further comprising a central inflatable member beneath the absorbent core.

20. The absorbent article of claim 1, wherein the central rising member comprises a central inflatable member.

21. The absorbent article of claim 1, wherein the central void passes completely through the outer absorbent member.

22. The absorbent article of claim 1, wherein the outer absorbent member comprises two spaced apart longitudinal strips of absorbent material having inner walls.

23. The absorbent article of claim 1, wherein the central absorbent member is unattached to the outer absorbent member in the target zone.

24. The absorbent article of claim 1, wherein the outer absorbent member is divided longitudinally into two discontiguous sections.

25. The absorbent article of claim 1, wherein the central rising member comprises a resilient material folded upon itself to have a thickness of at least two layers of the resilient material.

26. The absorbent article of claim 25, wherein the resilient material is folded to have a thickness of at least three layers of the resilient material.

27. The absorbent article of claim 1, wherein the central rising member comprises a resilient material folded to have an "e"-shaped cross-section.

28. The absorbent article of claim 1, wherein the central rising member comprises a resilient material folded to have a rotated "C"-shaped cross-section.

29. The absorbent article of claim 1, wherein the central rising member comprises a section of a resilient material having a flattened tube shape.

30. The absorbent article of claim 1, wherein the central rising member comprises a hinge element.

31. The absorbent article of claim 1, wherein deflection of the central rising member is maintained after release of the compression forces.

32. The absorbent article of claim 1, wherein the central rising member has a longitudinal centerline and can lift a load of 50 grams by at least 4 mm when the absorbent article is resting on a solid surface and the longitudinal sides of the absorbent article are laterally compressed toward the longitudinal centerline such that the longitudinal sides thereof together are brought no more than 13 mm toward the longitudinal centerline.

33. The absorbent article of claim 1, wherein the absorbent article is extensible.

34. The absorbent article of claim 1, further comprising restraint means such that the restraint means urge the article toward a relatively flat shape after the compression forces are relieved.

35. The absorbent article of claim 1, wherein the central absorbent member comprises an absorbent web having a width and the absorbent web is predisposed to deflect upward during laterally inward compression.

36. The absorbent article of claim 1, wherein the central rising member is contained within the central absorbent member.

37. The absorbent article of claim 35, further comprising a central absorbent pledget disposed beneath the absorbent web, the pledget having a width less than the width of the absorbent web.

38. The absorbent article of claim 35, wherein a portion of the absorbent web vertically overlaps a portion of the outer absorbent member in the target zone.

39. The absorbent article of claim 1, wherein the absorbent article exhibits an increase in Vertical Deformation in the target zone of at least about 20% relative to the Vertical Deformation in the target zone exhibited by an essentially identical absorbent article without a central rising member.

40. The absorbent article of claim 1, further comprising at least one attachment point attaching the central absorbent member to the backsheet.

41. An absorbent article for use on the body of a wearer, the article having a first end, a second end, two generally longitudinal sides, a top surface, a bottom surface, a thickness and a target zone, comprising:
 a) a liquid impervious backsheet;
 b) a liquid pervious topsheet attached to the backsheet;
 c) an absorbent core positioned between the topsheet and the backsheet, the absorbent core comprising:
  a central absorbent member having a width in the target zone;
  an outer absorbent member defining a central void open toward the top surface of the absorbent article for receiving at least a portion of the central absorbent member, the outer absorbent member having a width in the target zone greater than the width of the central absorbent member in the target zone; and
  a central inflatable member disposed within the central void adapted to deflect the central absorbent member away from the backsheet when activated by a wearer.

42. An absorbent article comprising a topsheet, a backsheet joined to the topsheet, an absorbent core disposed between the backsheet and the topsheet, the absorbent core comprising an outer absorbent member and a central absorbent member operatively associated with a central rising member, the central rising member having a garment-side surface, two generally longitudinal sides and a longitudinally central hinge dividing the central rising member into a first portion and second portion, the article further comprising attachment means in cooperative relationship with the central rising member, wherein application of inwardly lateral compressive force to the longitudinal sides of the central rising member causes the central rising member to deflect upward along the longitudinally central hinge, and wherein the attachment means holds the central rising member in an upwardly deflected state when the inwardly lateral compressive force is relaxed.

43. The absorbent article of claim 42, wherein the central rising member further comprises a garment-side surface, wherein the attachment means comprise a first attachment section on the garment-side surface of the first portion of the central rising member and a second attachment section on the garment-side surface of the second portion of the central rising member, wherein the first attachment section connects to the second attachment section when the garment-side surface of the first portion of the central rising member is brought into contacting relationship with the garment-side surface of the second portion of the central rising member.

44. The absorbent article of claim 42, wherein the attachment means comprises a mechanical attachment means disposed on the garment-side surface of the central rising member.

45. The absorbent article of claim 42, wherein the attachment means comprises hook-and-loop fasteners.

46. A method for producing an absorbent article having a central absorbent member, the method comprising:
  a) preparing an outer absorbent member, wherein the outer absorbent member has a central void;
  b) disposing a central absorbent member in the central void;
  c) disposing a central rising member beneath the central absorbent member;
  d) disposing a backsheet beneath the central rising member and beneath the outer absorbent member;
  e) disposing a topsheet above the central absorbent member and the outer absorbent member; and
  f) attaching the topsheet to the backsheet.

47. The method of claim 46, wherein the central rising member comprises an absorbent web of fibrous material.

48. The method of claim 46, wherein the outer absorbent member comprises two or more longitudinal strips of absorbent material.

49. The method of claim 46, wherein the central absorbent member overlaps the outer absorbent member.

50. A method for producing an absorbent article having a first end, a second end, two generally longitudinal sides, a top surface, a bottom surface and a thickness, comprising:
  a) preparing an outer absorbent member, wherein the outer absorbent member defines a central void open toward the top surface of the absorbent article;
  b) disposing a central rising member in the central void;
  c) inserting an absorbent material into the central void to form a central absorbent member, wherein the central rising member is adapted deflect the central absorbent member toward the top surface of the absorbent article upon the application of compression forces laterally to the generally longitudinal sides of the absorbent article.

51. The method of claim 50, further comprising:
  a) disposing a backsheet beneath the outer absorbent member;
  b) disposing a topsheet above the outer absorbent member; and
  c) attaching a portion of the topsheet to a portion of the backsheet.

52. The method of claim 50, wherein preparing the outer absorbent member with a central void comprises forming a layer of cellulosic fibers and forming the central void in a central portion of the layer.

53. The method of claim 50, wherein the central absorbent member comprises a cellulosic absorbent material.

54. The method of claim 50, wherein the central void in the outer absorbent member is formed by cutting out a section from the outer absorbent member, and wherein the central absorbent member comprises the cut-out section from the outer absorbent member.

55. An absorbent article having a first end, a second end, two generally longitudinal sides, a top surface, a bottom surface and a target zone, the absorbent article comprising:
  a) a backsheet;
  b) a topsheet attached to the backsheet; and
  c) an absorbent core positioned between the topsheet and the backsheet, the absorbent core including:
    a central absorbent member having a width in the target zone;
    an outer absorbent member having a width in the target zone greater than the width of the central absorbent member in the target zone, the outer absorbent member defining a central void with at least a portion of the central absorbent member received within the central void; and
    a central rising member disposed beneath the central absorbent member and above the backsheet, the central rising member effective to deflect the central absorbent member away from the backsheet upon application of compression forces laterally to the generally longitudinal sides of the absorbent article.

56. The absorbent article of claim 55, wherein the central void opens towards at least the top surface of the absorbent article.

57. The absorbent article of claim 55, wherein at least upon the application of compression forces laterally to the generally longitudinal sides of the absorbent article, the central rising member contacts the central absorbent member to effect the deflection of the central absorbent member away from the backsheet.

58. The absorbent article of claim 55, wherein the central rising member is absorbent.

59. The absorbent article of claim 55, wherein the central rising member comprises a fibrous mat.

60. The absorbent article of claim 55, wherein the central rising member is not absorbent.

61. The absorbent article of claim 55, wherein the central void passes completely through the outer absorbent member.

62. The absorbent article of claim 55, wherein the outer absorbent member comprises two spaced apart longitudinal strips of absorbent material having inner walls.

63. The absorbent article of claim 55, wherein the central absorbent member is unattached to the outer absorbent member in the target zone.

64. The absorbent article of claim 55, wherein the outer absorbent member is divided longitudinally into two discontiguous sections.

65. The absorbent article of claim 55, wherein the central rising member comprises a resilient material folded upon itself to have a thickness of at least two layers of the resilient material.

66. The absorbent article of claim 55, wherein the resilient material is folded to have a thickness of at least three layers of the resilient material.

67. The absorbent article of claim 55, wherein the central rising member comprises a resilient material folded to have an "e"-shaped cross-section.

68. The absorbent article of claim 55, wherein the central rising member comprises a resilient material folded to have a rotated "C"-shaped cross-section.

69. The absorbent article of claim 55, wherein deflection of the central rising member is maintained after release of the compression forces.

70. The absorbent article of claim 55, wherein the central rising member has a longitudinal centerline and can lift a load of 50 grams by at least 4 mm when the absorbent article is resting on a solid surface and the longitudinal sides of the absorbent article are laterally compressed toward the longitudinal centerline such that the longitudinal sides thereof together are brought no more than 13 mm toward the longitudinal centerline.

71. The absorbent article of claim 55, wherein the absorbent article is extensible.

72. The absorbent article of claim 55, wherein the central absorbent member comprises an absorbent web having a width and the absorbent web is predisposed to deflect upward during laterally inward compression.

* * * * *